United States Patent
Wu et al.

(10) Patent No.: US 9,187,558 B2
(45) Date of Patent: Nov. 17, 2015

(54) ANTI-EPITHELIAL CELL ADHESION MOLECULE (EPCAM) ANTIBODIES AND METHODS OF USE THEREOF

(71) Applicant: ACADEMIA SINICA, Taipei (TW)

(72) Inventors: Han-Chung Wu, Taipei (TW); Mei-Ying Liao, Taipei (TW); Cheng-Wei Lin, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 14/381,362

(22) PCT Filed: Mar. 1, 2013

(86) PCT No.: PCT/US2013/028667
§ 371 (c)(1),
(2) Date: Aug. 27, 2014

(87) PCT Pub. No.: WO2013/131001
PCT Pub. Date: Sep. 6, 2013

(65) Prior Publication Data
US 2015/0017230 A1   Jan. 15, 2015

Related U.S. Application Data

(60) Provisional application No. 61/606,220, filed on Mar. 2, 2012.

(51) Int. Cl.
| | | |
|---|---|---|
| *A61K 39/395* | (2006.01) | |
| *C07K 16/18* | (2006.01) | |
| *C07K 16/30* | (2006.01) | |
| *G01N 33/574* | (2006.01) | |
| *A61K 39/00* | (2006.01) | |

(52) U.S. Cl.
CPC ............. *C07K 16/18* (2013.01); *C07K 16/30* (2013.01); *G01N 33/574* (2013.01); *A61K 2039/505* (2013.01); *C07K 2317/24* (2013.01); *C07K 2317/34* (2013.01); *C07K 2317/56* (2013.01); *C07K 2317/565* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 8,318,911 B2 * | 11/2012 | Anastasi et al. ........... 530/388.1 |
| 2007/0243201 A1 | 10/2007 | Loibner et al. |
| 2010/0092491 A1 | 4/2010 | Anastasi et al. |
| 2010/0311954 A1 * | 12/2010 | Chamberlain et al. ..... 530/387.3 |
| 2011/0165161 A1 | 7/2011 | Lin et al. |

FOREIGN PATENT DOCUMENTS

| | | |
|---|---|---|
| WO | 98/46645 A2 | 10/1998 |
| WO | 2011/032296 A1 | 3/2011 |
| WO | 2011/079283 A1 | 6/2011 |

OTHER PUBLICATIONS

Bluemel et al. "Epitope distance to the target cell membrane and antigen size determine the potency of T cell-mediated lysis by BiTE antibodies specific for a large melanoma surface antigen" Cancer Immunol Immunother (2010) 59:1197-1209.

* cited by examiner

*Primary Examiner* — Sheela J Huff
(74) *Attorney, Agent, or Firm* — Hsiu-Ming Saunders; Intellectual Property Connections, Inc.

(57) ABSTRACT

An isolated monoclonal antibody or an antigen-binding fragment thereof is disclosed. The antibody or the antigen-binding fragment is characterized by: (a) having a specific binding affinity to epithelial cell adhesion molecule (EpCAM) comprising the amino acid sequence of SEQ ID NO: 1; (b) having a specific binding affinity to cancer cells expressing EpCAM said cancer cells being selected from the group consisting of oral cancer cells, nasopharyngeal cancer cells (NPC), colorectal cancer cells, and ovarian cancer cells; and (c) having no binding affinity to human umbilical vein endothelial cell (HUVEC) and normal nasal mucosal epithelia (NNM). Also disclosed is an isolated monoclonal antibody or an antigen-binding fragment thereof that has a specific binding affinity to an epitope within the sequence of KPEGALQNNDGLYDP-DCDE (SEQ ID NO: 63) located within the EGF-like domain II of epithelial cell adhesion molecule (EpCAM). Methods of using the same are also disclosed.

20 Claims, 17 Drawing Sheets

FIG. 7

A V_H (SEQ ID NO: 24)

| | FW1 | | CDR1 (4) | FW2 | CDR2 |
|---|---|---|---|---|---|
| hEpAb2-6 V_H | VKLQESGPELKKPGETVKISCKAS (SEQ ID NO: 18) | | GYTFTDYSMH | WVKQAPGKGLKWMGW (11) | INTETGEP (5) |
| | FW3 | | CDR3 | FW4 | |
| hEpAb2-6 V_H | TYADDFKGRFAFSLETSASTAYLQINNLKNEDTATYFCAR (SEQ ID NO: 19) | | TAVY (6) | WGQGTTVTVSS (SEQ ID NO: 20) | |

V_L (SEQ ID NO: 25)

| | FW1 | | CDR1 | FW2 | CDR2 |
|---|---|---|---|---|---|
| hEpAb2-6 V_L | DIQMTQSPSSLSASLGERVSLTC (SEQ ID NO: 21) | | RASQEISVSLS (7) | WLQQEPDGTIKRLIY (22) | ATSTLDS (8) |
| | FW3 | | CDR3 | FW4 | |
| hEpAb2-6 V_L | GVPKRFSGSRSGSDYSLTISSLESEDFVDYYC (SEQ ID NO: 23) | | LQYASYPWT (9) | FGGGTKLEIKRADAAPTVS (17) | |

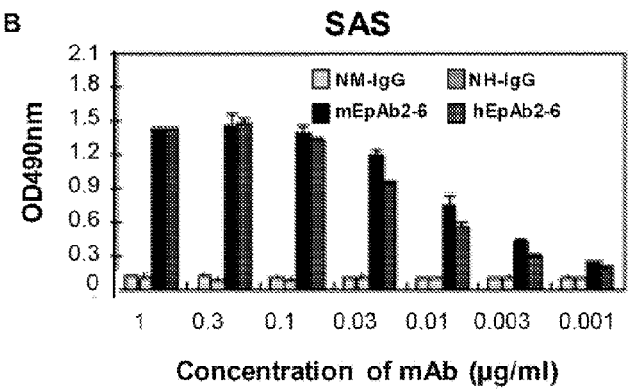

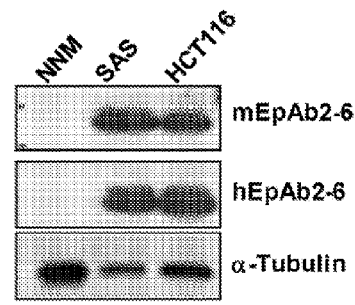

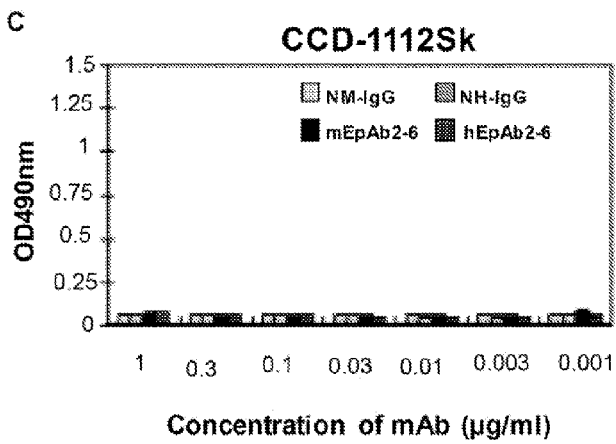

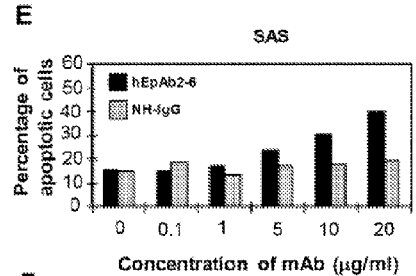

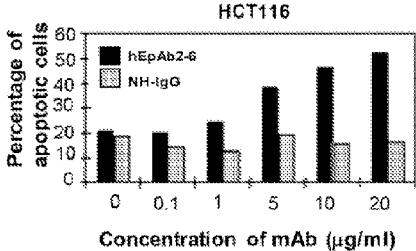

FIG. 11
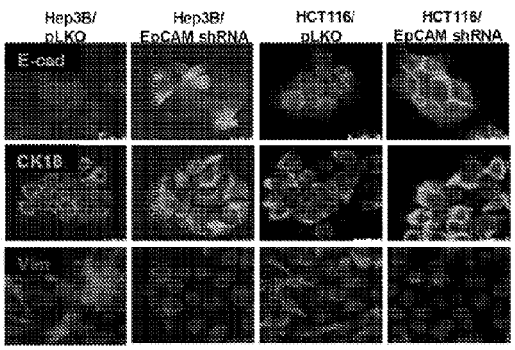
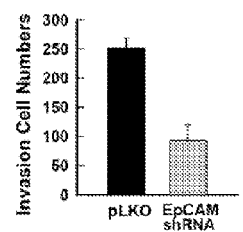
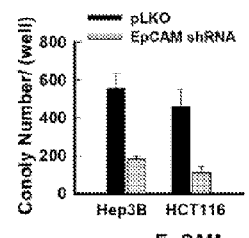
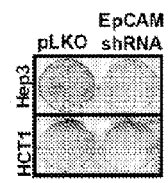
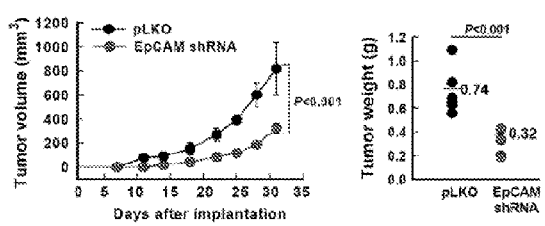
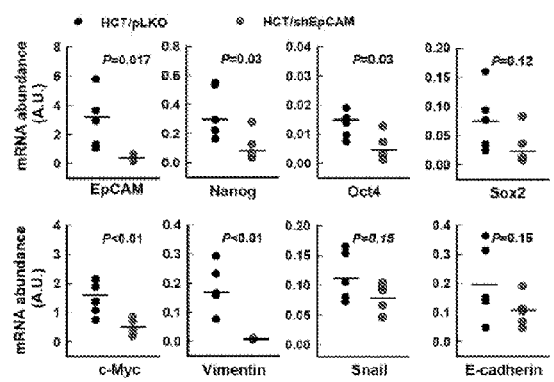

FIG. 15

Summary of the main features of mAbs against cancer cells

| mAb clone | ELISA | WB | Flow | Isotype | Cell lines | | | | | | | | | | | | |
|---|---|---|---|---|---|---|---|---|---|---|---|---|---|---|---|---|---|
| | | | | | SAS | NPC | HCT 116 | Matha yu | PaCa | CL1-5 | PC3 | HTB10 | A498 | SKOV3 | U2OS | HUV EC | NN M |
| OCAb1-1 | + | + | + | IgM,κ | +++ | + | − | − | − | − | +/− | − | − | − | − | ++ | − |
| OCAb2-6 | + | + | + | IgG2a, κ | +++ | − | − | − | − | − | − | − | − | − | − | − | − |
| OCAb3-3 | + | + | + | IgG1, κ | +++ | + | − | + | + | − | + | + | +/− | ++ | − | − | − |
| OCAb4-10 | + | + | + | IgG1, κ | +++ | − | − | − | − | − | − | − | − | − | − | − | − |
| OCAb5-5 | + | + | + | IgG2a, κ | +++ | − | − | − | − | − | − | − | − | − | − | − | − |
| OCAb6-1 | + | + | + | IgG2a, κ | +++ | − | − | − | − | − | − | − | − | − | − | − | − |
| OCAb7-1 | + | − | − | IgG1, κ | ++ | + | + | − | − | − | − | − | − | − | − | − | − |
| OCAb8-6 | + | + | + | IgG1, κ | ++ | + | − | − | − | − | − | − | − | + | − | − | − |
| OCAb9-1 | + | + | − | IgG1, κ | +++ | − | − | − | − | − | − | − | − | + | − | − | − |
| OCAb10-1 | + | + | + | IgG2a, κ | +++ | + | − | − | + | +/− | + | − | − | + | − | − | − |
| OCAb11-3 | + | + | − | IgG1, κ | +++ | − | − | − | − | + | +/− | − | − | + | − | − | − |
| OCAb12-1 | + | + | − | IgG1,2a, κ | +++ | +/− | − | − | − | − | − | − | − | − | − | − | − |

Abbreviation: +, represent binding (+++, OD 490nm >1.5; ++, OD 490nm 1-1.5; +, OD 490nm 0.5-1; +/−, OD 490nm 0.2-0.5 ); −, represent no binding (OD 490nm <0.2).

FIG. 16

Summary of the main features of anti-EpCAM mAbs

| mAb clone | ELISA | WB | Flow | Isotype | Cell lines | | | | | |
|---|---|---|---|---|---|---|---|---|---|---|
| | | | | | SAS | NPC | HCT116 | SKOV3 | HUVEC | NNM |
| OCAb9-1 | + | + | + | IgG1, κ | ++ | + | + | + | − | − |
| EpAb1-3 | + | + | + | IgG1, κ | ++ | + | +/− | + | − | − |
| EpAb2-6 | + | + | + | IgG2a, κ | +++ | ++ | + | +/− | − | − |
| EpAb3-5 | + | + | + | IgG2b, κ | +++ | ++ | + | ++ | − | − |
| EpAb4-1 | + | + | + | IgG1, κ | ++ | ++ | + | + | − | − |
| EpAb5-4 | + | + | + | IgG1, κ | ++ | + | +/− | + | − | − |

Abbreviation: +, represent binding (+++, OD 490nm >1.5; ++, OD 490nm 1-1.5; +, OD 490nm 0.5-1; +/−, OD 490nm 0.2-0.5); −, represent no binding (OD 490nm <0.2).

FIG. 17

Amino acid sequence of $V_H$ and $V_L$ domains of EpAb2-6

$V_H$ domains (SEQ ID NO: 2)

|  | FW1 | CDR1 | FW2 | CDR2 |
|---|---|---|---|---|
| EpAb2-6 | EVQLVESGPELKKPGETVKISCKAS<br>(SEQ ID NO: 10) | GYTFTDYSMH<br>(SEQ ID NO: 4) | WVKQAPGKGLKWMGW<br>(SEQ ID NO: 11) | INTETGEP<br>(SEQ ID NO: 5) |
|  | FW3 | CDR3 | FW4 | Family |
|  | TFADDFKGRFAFSLETSARTTYLQINNLKNEDTATYFCAR<br>(SEQ ID NO: 12) | TAVY<br>(SEQ ID NO: 6) | WGQGTSLTVSS<br>(SEQ ID NO: 13) | $V_H9$ |

$V_L$ domains (SEQ ID NO: 3)

|  | FW1 | CDR1 | FW2 | CDR2 |
|---|---|---|---|---|
| EpAb2-6 | DIQLTQSPSSLSASLGERVSLTC<br>(SEQ ID NO: 14) | RASQEISVSLS<br>(SEQ ID NO: 7) | WLQQKPDGTIKRLIY<br>(SEQ ID NO: 15) | ATSTLDS<br>(SEQ ID NO: 8) |
|  | FW3 | CDR3 | FW4 | Family |
|  | GVPKRFSGSRSGSDYSLTISSLESEDFADYYC<br>(SEQ ID NO: 16) | LQYASYPWT<br>(SEQ ID NO: 9) | FGGGTKLEIKRADAAPTVS<br>(SEQ ID NO: 17) | $V_K9$ |

Complementarity-determining regions 1-3 (CDR1-3), and framework regions 1-4 (FW1-4) for both the $V_H$ and $V_L$ domains are shown. The V domain families were aligned by VBASE2 database.

FIG. 18

Kinetic constants and binding affinities of anti-EpCAM mAbs

| mAb colon | $K_d(M)$ | $K_{on}(M^{-1}S^{-1})$ | $K_{off}(S^{-1})$ |
|---|---|---|---|
| OCAb9-1 | $7.168 \times 10^{-11}$ | $3.284 \times 10^{6}$ | $2.354 \times 10^{-4}$ |
| EpAb1-3 | $1.833 \times 10^{-9}$ | $1.849 \times 10^{5}$ | $3.389 \times 10^{-4}$ |
| EpAb2-6 | $3.491 \times 10^{-10}$ | $4.007 \times 10^{5}$ | $1.399 \times 10^{-4}$ |
| EpAb3-5 | $\leq 4.66 \times 10^{-13}$ | $2.961 \times 10^{6}$ | $1.38 \times 10^{-6}$ |
| EpAb4-1 | $1.228 \times 10^{-12}$ | $2.865 \times 10^{5}$ | $3.519 \times 10^{-7}$ |
| EpAb5-4 | $2.431 \times 10^{-10}$ | $6.221 \times 10^{5}$ | $1.513 \times 10^{-4}$ |
| hEpAb2-6 | $6.773 \times 10^{-10}$ | $3.756 \times 10^{5}$ | $2.544 \times 10^{-4}$ |

$K_{on}$ and $K_{off}$ were measured by SRP in a BIAcore using purified mAb, and the $K_d$ was calculated by BIAevaluation software.

FIG. 19

Alignment of phage-displayed peptide sequences selected by EpAb2-6

| Clone | Phage sequence |
|---|---|
| PC-26 | H G T Q M T W W D P D L |
| PC-11,-29 |       M Q G K D W M D L S P T |
| PC-3,-4,-18 | S T Q M S Y R D Q D L Y |
| PC-12 | V P M S R P E W N D L Y |
| PC-1,-19,-27,-35 | V P V G R L D F I D L Y |
| PC-21,-37 |    T Q K M D A H D L Y P V |
| PC-20 |       F Q V G D L Y D H M W N |
| PC-2,-7,-8 |       W Q N V E Y D M R E W I |
| PC-44 | V T P Q A K D W Y T L Y |
| EpCAM₈₃₋₁₀₀ | K P E G A L Q N N D G L Y D P D C D E |

NOTE. Consensus amino acids are indicated by boldface type.

ANTI-EPITHELIAL CELL ADHESION MOLECULE (EPCAM) ANTIBODIES AND METHODS OF USE THEREOF

REFERENCE TO RELATED APPLICATION

This application is a national stage application (under 35U.S.C 371) of PCT/US2013/028667 filed on 1 Mar. 2013, which claims priority to U.S. provisional application 61/606,220 filed on 2 Mar. 2012, all of which are herein incorporated by reference in their entireties.

FIELD OF THE INVENTION

The present invention relates generally to anti-cancer agent, and more specifically to antibodies for treatment, diagnosis and imaging of cancer.

BACKGROUND OF THE INVENTION

Head and neck squamous cell carcinoma (HNSCC) is the sixth most common malignancy in the world in developed countries. Oral squamous cell carcinoma (OSCC) is the most common cancer of the head and neck region. Despite significant improvements in diagnosis, local management, and chemotherapy of head and neck cancer, there has been no significant increase in long-term survival rates over the past 30 years. The overall mortality rate for intra-oral cancer remains high at approximately 50%, even with modern medical services. Therefore, prevention and early diagnosis and treatment of high-risk pre-malignant lesions are instrumental in the reduction of HNSCC related deaths.

SUMMARY OF THE INVENTION

In one aspect, the invention relates to a purified or an isolated monoclonal antibody or an antigen-binding fragment thereof that has a specific binding affinity to an epitope within the sequence of KPEGALQNNDGLYDPDCDE (SEQ ID NO: 63) located within the EGF-like domain II of epithelial cell adhesion molecule (EpCAM; SEQ ID NO: 1).

In one embodiment of the invention, the antibody or antigen-binding fragment exhibits the following characteristics: the aforementioned binding affinity is abrogated when Tyrosine (Y) at amino acid position 95, or Aspartic acid (D) at amino acid position 96, or said Y and said D, within the EGF-like domain II of EpCAM are mutated (or have substituted mutations).

In another embodiment of the invention, the antibody or antigen-binding fragment comprises:

(a) a heavy chain variable region, comprising: (i) complementarity determining region 1 (CDR1) comprising SEQ ID NO: 4; (ii) complementarity determining region 2 (CDR2) comprising SEQ ID NO: 5; and (iii) complementarity determining region 3 (CDR3) comprising SEQ ID NO: 6; and (b) a light chain variable region, comprising: (i) CDR1 comprising SEQ ID NO: 7; (ii) CDR2 comprising SEQ ID NO: 8; and (iii) CDR3 comprising SEQ ID NO: 9.

In another embodiment of the invention, the binding fragment comprises an Fv fragment of the antibody. Alternatively, the binding fragment may comprise an Fab fragment of the antibody.

In another embodiment of the invention, the antibody is a humanized monoclonal antibody.

In another embodiment of the invention, the heavy chain variable region comprises the amino acid sequence of SEQ ID NO: 24, and the light chain variable region comprises the amino acid sequence of SEQ ID NO: 25.

In another aspect, the invention relates to a purified or an isolated single-chain variable fragment, which comprises:

(a) a heavy chain variable region comprising the amino acid sequence of SEQ ID NO: 2 and a light chain variable region comprising the amino acid sequence of SEQ ID NO: 3, or a heavy chain variable region comprising the amino acid sequence of SEQ ID NO: 24 and a light chain variable region comprising the amino acid sequence of SEQ ID NO: 25; and (b) a linker peptide connecting the heavy chain variable region and the light chain variable region.

Further in another aspect, the invention relates to an isolated monoclonal antibody or an antigen-binding fragment thereof, which exhibits the following characteristics:

(a) having a specific binding affinity to epithelial cell adhesion molecule (EpCAM) comprising the amino acid sequence of SEQ ID NO: 1;

(b) having a specific binding affinity to cancer cells expressing EpCAM, said cancer cells being selected from the group consisting of oral cancer cells, nasopharyngeal cancer cells, colorectal cancer cells, and ovarian cancer cells; and (c) having no binding affinity to human umbilical vein endothelial cell and normal nasal mucosal epithelia.

In one embodiment of the invention, said antibody or antigen-binding fragment exhibits a characteristic of inducing apoptosis of said cancer cells and/or inhibiting growth of said cancer cells in vivo.

In another embodiment of the invention, said antibody or antigen-binding fragment exhibits a specific binding affinity to an epitope within the sequence of KPEGALQNNDGLYDPDCDE (SEQ ID NO: 63) located within the EGF-like domain II of EpCAM.

In another embodiment of the invention, said antibody or antigen-binding fragment is labeled by a detectable compound or an enzyme, or is encapsulated within a liposome.

In another embodiment of the invention, the antibody or antigen-binding fragment comprises:

(a) a heavy chain variable region comprising the amino acid sequence of SEQ ID NO: 2 and a light chain variable region comprising the amino acid sequence of SEQ ID NO: 3; or (b) a heavy chain variable region comprising the amino acid sequence of SEQ ID NO: 24 and a light chain variable region comprising the amino acid sequence of SEQ ID NO: 25.

Further in another aspect, the invention relates to a composition comprising: (a) an isolated antibody or antigen-binding fragment as aforementioned; (b) an anti-cancer agent; and (c) a pharmaceutically acceptable carrier.

Further in another aspect, the invention relates to a method of inhibiting growth of cancer cells and/or tumor-initiating cells, the method comprising administering to a subject in need thereof a composition that comprises: (a) an antibody or antigen-binding fragment thereof as aforementioned; and (b) a pharmaceutically acceptable carrier, wherein said cancer cells and/or tumor-initiating cells express EpCAM.

In one embodiment of the invention, a humanized antibody or antigen-binding fragment is administered to the subject. The cancer cells may be selected from the group consisting of oral cancer cells, nasopharyngeal cancer cells, colorectal cancer cells, and ovarian cancer cells.

Yet in another aspect, the invention relates to a method of detecting and/or diagnosing cancer that expresses EpCAM, the method comprising:

(a) obtaining a cell or a tissue sample from a patient;

(b) contacting the cell or the tissue sample with the antibody or binding fragment as aforementioned;

(c) assaying the binding of the antibody or binding fragment to the cell or tissue sample; and (d) comparing the binding with a normal control to determine the presence of the cancer that expresses EpCAM in the subject.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 7 shows the development of Humanized Antibody Against EpCAM. The CDRs of EpAb2-6 were grafted onto human IgG1 backbone to create humanized EpAb2-6 (hEpAb2-6) (A). Binding activity of hEpAb2-6 to human cancer cell lines. ELISA measured the binding activity of mEpAb2-6 and hEpAb2-6 to SAS (B) and CCD-1112Sk (C) cells. Normal mouse IgG (NM-IgG) and normal human IgG (human IgG) was used as a negative control. (D) Western blot analysis of mEpAb2-6 and hEpAb2-6 against NNM, SAS, and HCT116 cells. SAS (E) and HCT116 (F) cells were treated with hEpAb2-6 (0-20 µg/ml) for 6 h, and cell death was measured by flow cytometry with Annexin-V FITC and P1 double staining.

FIG. 11 shows expression of EpCAM is Associated with EMT Progression and Tumorigenesis. (A) Immunofluorescence staining of E-cadherin (E-cad), cytokeratin 18 (CK18), and vimentin (Vim) in EpCAM knockdown Hep3B and HICT116 cells. (B) Real-time qPCR (left) and Western blot (right) analyses of EMT gene expression in EpCAM-knockdown Hep3B and HCT116 cells. (C) Real-time qPCR analysis of EMT gene expression in EpCAM-high and -low sorted cells. (D and E) Suppression of EpCAM inhibits invasion (D) and colony formation (E) of tumor cells in vitro. (F) Suppression of EpCAM reduces tumor growth in vivo. Subcutaneous injected with $2 \times 10^6$ of HCT/LKO and HCT/EpCAM shRNA cells into NOD/SCID mice, tumor volumes were measured every 3 day (left) and tumor weights were measured at the end of the experiments (right) (n=6). (G) RNA from tumor extractions was analyzed by real-time qPCR (data were presented as mean±SD, and p value was analyzed by I-test).

FIG. 14D shows cellular localization of EpICD expresses in membrane (M), cytosol (C), and nucleus (N). Right image is shown in enlarged local view from boxed region of the left image. Expressions of EpCAM, c-Myc, Nanog, Oct4, and Sox2 mRNA level in 42 human colon cancer patient were determined by qPCR analysis. Correlation between EpCAM and reprogramming genes was evaluated by Speannan's analysis (E).

FIG. 15 is a summary of the main features of mAbs against cancer cells.

FIG. 16 is a summary of the main features of anti-EpCAM mAbs.

FIG. 17 shows the amino acid sequence of $V_H$ and $V_L$ domains of EpAb2-6.

FIG. 18 shows kinetic constants and binding affinities of anti-EpCAM mAbs.

FIG. 19 shows alignment of phage-displayed peptide sequences (SEQ ID Nos. 64-73) selected by EpAb2-6.

DETAILED DESCRIPTION OF THE INVENTION

Definitions

Figure 1:
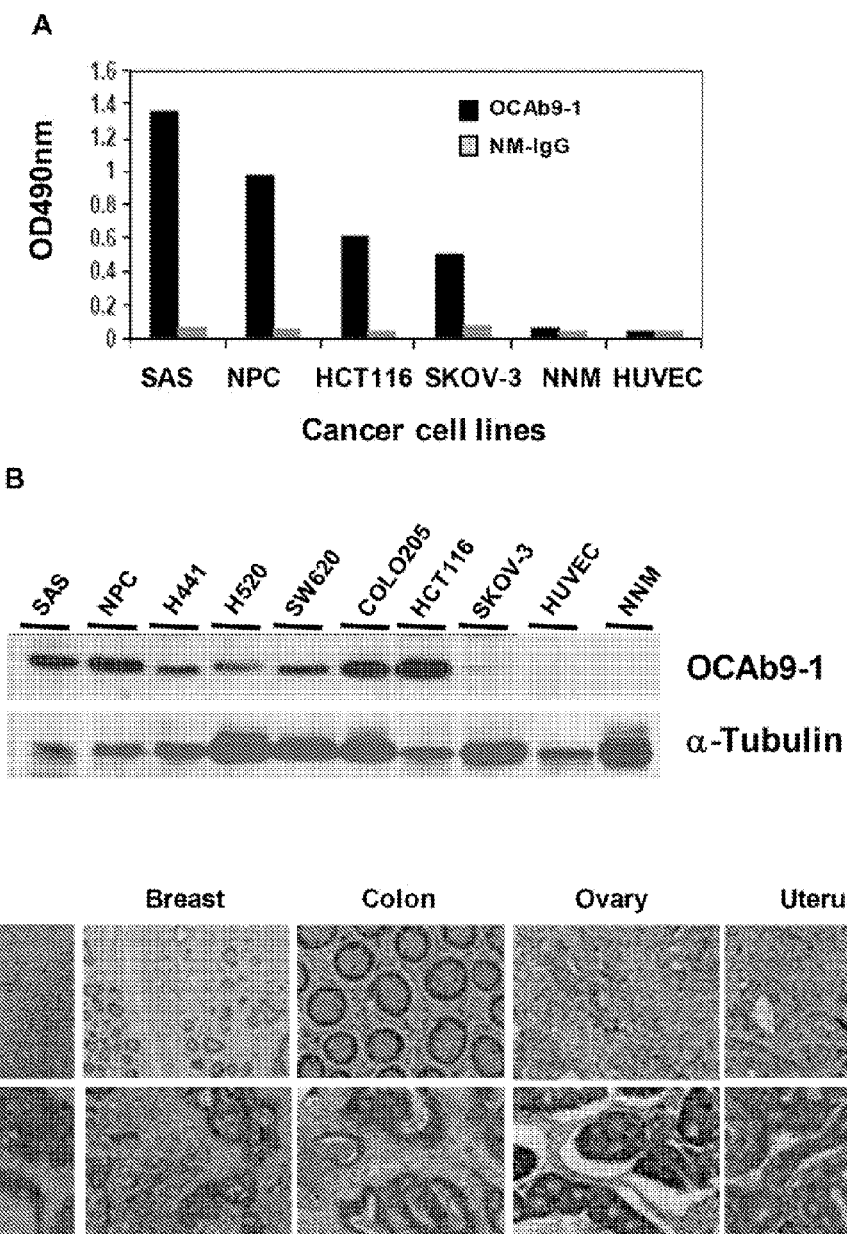
FIG. 1 shows the binding Activity of OCAb9-1 to Various Cancer Cell Lines. (A) ELISA analysis of the binding activity of OCAb9-1 in various cancer cell lines. NM-IgG was used as a control. (B) Western blot analysis of OCAb9-1 mAb against oral cancer (SAS), nasopharyngeal carcinoma (NPC), lung cancer (H1441 and H520), colorectal cancer (HICT116, SW620 and COLO 205), ovarian cancer (SKOV-3), human umbilical vein endothelial cell (HUVEC), and normal nasal mucosal epithelia (NNM). (C) Immunohistochemical staining of anti-EpCAM mAb (OCAb9-1) in human tissue array. Paraffin-embedded sections were incubated with OCAb9-1 to detect EpCAM expression in different human cancer tissues, including oral, breast, colon, ovary, pancreas, and uterus, and their matched normal tissues. EpCAM (stained brown); hematoxylin (stained blue) used as background staining. Cell images were acquired at 200× magnification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

Abbreviations: mAb, monoclonal antibodies; NNM, Normal nasal mucosal; FACS, flow cytometric analysis; ELISA, Enzyme-linked immunosorbent assay; EMT, epithelial-mesenchymal transition; Quantitative Reverse Transcription Polymerase Chain Reaction (RT-PCR); ChIP, Chromatin Immunoprecipitation; GAPDH, glyceraldehyde-3-phosphate dehydrogenase; HUVEC, Human Umbilical Vein Endothelial Cells; IHC, immunohistochemistry; CDR, complementarity-determining region.

As used herein, "preparation" shall generally mean something prepared, manufactured, a substance especially prepared.

As used herein, the term "antibody" means an immunoglobulin (Ig) molecule or a fragment of an immunoglobulin molecule having the ability to specifically bind to a particular antigen. The Ig monomer is a "Y"-shaped molecule that consists of four polypeptide chains; two identical heavy chains and two identical light chains connected by disulfide bonds. The arms of the Y, for example, contain the site that bind antigen and, therefore, recognize specific foreign objects. This region of the antibody is called the Fab (fragment, antigen binding) region.

As used herein, the term "antibody" means not only full-length antibody molecules but also fragments of antibody molecules retaining antigen binding ability. Such fragments are also well known in the art and are regularly employed both in vitro and in vivo. The term "antibody" means not only full-length immunoglobulin molecules but also antigen binding active fragments such as the well-known active fragments F(ab')$_2$, Fab, Fv, and Fd.

The fragment antigen-binding (Fab fragment) is a region on an antibody that binds to antigens. It is composed of one constant and one variable domain of each of the heavy and the light chain. The two variable domains bind the epitope on their specific antigens. Fc and Fab fragments can be generated in the laboratory. The enzyme papain can be used to cleave an immunoglobulin monomer into two Fab fragments and an Fc fragment. The enzyme pepsin cleaves below hinge region, so a F(ab')$_2$ fragment and a pFc' fragment is formed. The enzyme IdeS (Immunoglobulin degrading enzyme from *Streptococcus pyogenes*, trade name FabRICATOR™) cleaves IgG in a sequence specific manner at neutral pH. The F(ab')$_2$ fragment can be split into two Fab' fragments by mild reduction.

The variable domain of an antibody is referred to as the Fv region and is the most important region for binding to antigens.

An "Fv fragment" is an active antibody fragment (Fv) composed of the variable portions of heavy and light chains. The "Fv fragment" consists of the heavy chain variable domain (VFI) and the light chain variable domain (VL) held together by strong noncovalent interaction. Thus, each Fv fragment contains one intact antigen-binding site and represents the minimal active fragment derivable from an antibody molecule.

The variable regions of the heavy and light chains can be fused together to form a single-chain variable fragment (scFv), which is only half the size of the Fab fragment, yet retains the original specificity of the parent immunoglobulin.

It has been reported that "fully" human antibodies may avoid some of the side effects of humanized and chimeric antibodies. Two successful approaches were identified—phage display-generated antibodies and mice genetically engineered to produce more human-like antibodies. Phage display could be used such that variable antibody domains could be expressed on filamentous phage antibodies.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or FcipFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of full-length antibodies with antigen-binding ability, are often referred to as "chimeric" antibodies. Such chimeric antibodies may be produced in which some or all of the FR regions of the antibody have been replaced by other homologous human FR regions.

Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries. The techniques of Cole et al. and Boerner et al. are also available for the preparation of human monoclonal antibodies (Cole et al., Monoclonal Antibodies and Cancer Therapy, Alan R. Liss, p. 77(1985) and Boerner et al., J. Immunol., 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016. Such fully human or humanized monoclonal antibodies will have particular utility in that they will not evoke an immune response against the antibody itself. See U.S. Pat. No. 7,622,113, which is herein incorporated by reference in its entirety.

The antibody may be labeled and may be immobilized on a solid support. The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods

Cell Lines and Culture. The following human cell lines were used: oral cancer (FaDu and SAS), nasopharyngeal carcinoma (NPC039), ovarian cancer (SKOV-3), lung cancer (CL1-5, H441 and H520), pancreatic cancer (MIA PaCa-2), colorectal cancer (COLO 205, HCT116 and SW620), hepatocellular carcinoma (Hep3B and Mahlavu), renal cell carcinoma (A498), prostate cancer (PC3). CCD-1112Sk (human normal foreskin) and primary culture of normal nasal mucosal epithelia (NNM). NPC were established in our laboratory (Lin et al. (1993) "Characterization of seven newly established nasopharyngeal carcinoma cell lines" Lab. Invest. 68, 716-727). Mahlavu were obtained courtesy of Dr. Michael Hsiao (Genomic Research Center, Academia Sinica). Primary culture of normal nasal mucosal epithelia (NNM) were adopted from surgery of patients with nasal polyposis (Lee et al., (2007) "Effect of Epstein-Barr virus infection on global gene expression in nasopharyngeal carcinoma" Funct. Integr. Genomics 7, 79-93). Human umbilical vein endothelial cells (HUVECs) were purchased (Lonza, Walkersville, Md.) and were grown in EBM-2 medium (Lonza, Walkersville, Md.). Human oral cancer cell line SAS was obtained from the Japanese Collection of Research Bioresources (Tokyo, Japan). The cells were cultivated in 5% $CO_2$ at 37° C. in Dulbecco modified Eagles' medium (DMEM) supplemented with 10% FBS. Lung adenocarcinoma cell line (CL 1-5) (Chu et al., (1997) "Selection of invasive and metastatic subpopulations from a human lung adenocarcinoma cell line" Am J Respir Cell Mol Biol. 17, 353-60) provided by Dr. Pan-Chyr Yang was cultured in RPMI medium supplemented with 10% FBS. Other cell lines were purchased from ATCC and were cultured in Dulbecco's Modified Eagle's medium (DMEM) supplemented with 5% or 10% fetal bovine serum (FBS) at 37° C. in a humidified incubator containing 5% $CO_2$. These cells were cultured by ATCC's protocols and had been passaged for fewer than 6 months after resuscitation. FaDu (pharynx carcinoma).

Generation of Monoclonal Antibodies and Purification of IgG. Monoclonal antibodies against SAS cells and EpCAM antigens were generated following a standard procedure with slight modifications (Wu et al. (2003). "Identification of a dengue virus type 2 (DEN-2) serotype-specific B-cell epitope and detection of DEN-2-immunized animal serum samples using an epitope-based peptide antigen" J. Gen. Virol. 84, 2771-2779; Liu et al. (2011) "Molecular mimicry of human endothelial cell antigen by autoantibodies to nonstructural protein 1 of dengue virus" J. Biol. Chem. 286, 9726-36). Briefly, female BALB/cJ mice were immunized intraperitoneally with SAS four times at 3-week intervals. On day 4 after the final boost, splenocytes were harvested from the immunized mouse spleen and fused with NSI/1-Ag4-1 myeloma cells by 50% polyethylene glycol (GIBCO, CA, USA). Fused cells were suspended in DMEM supplemented with hypoxanthine-aminopterin-thymidine (HAT) (SIGMA™, St. Louis, Mo.) and hybridoma cloning factor (ICN, Aurora, Ohio) and then plated in 96-well plates. These hybridomas, which were positive for SAS but negative for NNM, were then subcloned by limited dilution and preserved in liquid nitrogen. Ascites were produced in pristane-primed BALB/cJ mice and mAbs purified with protein G Sepharose 4G gel (GE Healthcare Biosciences, Pittsburgh, Pa.).

ELISA. 96-well plates (Corning Costar, St. Louis, Mo.) were seeded with SAS (oral carcinoma), NPC, HCT116 (colon cancer), SKOV3 (ovarian cancer cell line), NNM and HUVEC cells. The plates fixed with 2% paraformaldehyde and blocked with 1% bovine serum albumin. OCAb9-1 was added to the plates and incubated for 1 h. The plates were then washed with PBS containing 0.1% (w/v) TWEEN® 20 ($PBST_{0.1}$) and incubated with horseradish peroxidase-conjugated anti-mouse IgG (Jackson ImmunoResearch Laboratories) for another 1 h. After washing, the plates were incubated with substrate solution o-phenylenediamine dihydrochloride (SIGMA™). The reaction was stopped by adding 3 N HCl, and the plates were read using a microplate reader at 490 nm.

Flow Cytometry. SAS, HCT116 and NNM were dissociated with 0.25% trypsin-EDTA (1 mM) (INVITROGEN®) for 1-3 min. Cells were washed with fluorescence-activated cell sorting buffer (PBS containing 1% fetal calf serum) and then incubated for 1 h at 4° C. in fluorescence-activated cell sorting buffer with the OCAb9-1 and EpAb mAbs at dilutions that ranged from 0.00001 to 1 g/ml. Phycoerythrin-conjugated goat anti-mouse IgG was used as a secondary antibody (dilution 1:250; Jackson ImmunoResearch Laboratories (West Grove, Pa.) for 30 min at 4° C. After the final wash, the cells were re-suspended with 1% FBS in PBS and analyzed by flow cytometry (BD, San Jose, Calif.).

Immunofluorescent Staining. Cells cultured on cover slips were fixed in paraformaldehyde, washed, and then blocked with 1% bovine serum albumin in PBS for 10 min. Cells were incubated at room temperature with primary antibodies in 1% bovine serum albumin. After 1 h incubation, cells were washed and incubated with fluorescein isothiocyanate (FITC) goat anti-mouse antibody (Jackson ImmunoResearch Laboratories), Alexafluor488 goat-anti-mouse or Alexaflour568 goat-anti-rabbit (INVITROGEN®) antibodies. 4',6-Diamidino-2-phenylindole (DAPI) was added for nuclear counter staining.

Immunohistochemistry Assay. Tumor tissues from mice or human tissue arrays (Pantomics Inc., San Franscico, Calif.) were incubated with antibodies and then with horseradish peroxidase (HRP)-conjugated secondary antibody. The sections were finally incubated with diaminobenzidine and counterstained with hematoxylin. Human colon cancer tissue microarray and 15 major types of cancer tissue assay (TMA BC05011 and TMA MTU391) were purchased from BIOMAX®. The expression of EpICD was quantified using HistoQuest software (TissueGnostics, Vienna, Austria). Standardized automatic acquisition was performed by AQuest software (TissueGnostics, Vienna, Austria) with controlling filters, camera, and motor stage (Marzhiuser, Wetzlar, Germany). For image cytometry, all images were obtained using Tissue-Faxs software (TissueGnostics, Vienna, Austria).

Identification of the Target Protein. SAS cells were lysed with lysis buffer (50 mM Tris-HCl, pH 7.4, 150 mM NaCl, 1% NP-40) supplemented with a protease inhibitor cocktail tablet (Roche, Indianapolis, Ind.). The supernatant was applied to protein G sepharose (GE Healthcare Biosciences, Pittsburgh, Pa.) coupled with OCAb9-1. After washing, the proteins bound to OCAb9-1 were eluted with elution buffer (0.2 M Glycine, pH 2.5, 150 mM NaCl, and 1% NP-40), and the eluates were neutralized with 1 M Tris-HCl, pH 9.1 (Liu et al., 2011). The eluates were separated by SDS-PAGE. The band of interest was cut from the gel, reduced with 50 mM dithioerythreitol (DTE) in 25 mM ammonium bicarbonate (ABC) at pH 8.5 for 1 hr at 37° C., and alkylated with 100 mM iodoacetamide (IAA) in ABC for 1 hr at RT. After washing with 50% acetonitrile in ABC, the gel was soaked in 100% acetonitrile and incubated with 0.02 µg trypsin for 16 hrs at 37° C. The digested peptides were extracted with 50% acetonitrile in 5% TFA and were concentrated using a Concentrator (Eppendorf, Hamburg, Germany). The sample was analyzed by LC-MS/MS sequencing in the Core Facility for Proteomics and Structural Biology Research at Academia Sinica.

Immunoprecipitation and Western Blot Analysis. Cells were extracted with RIPA buffer (0.01 M sodium phosphate (pH 7.2), 150 mM NaCl, 2 mM EDTA, 50 mM NaF, 1% Nonidet P-40, 1% sodium deoxycholate, and 0.1% SDS), supplemented with a protease inhibitor mixture tablet (Roche, Indianapolis, Ind.) and spun at 20,000 g for 30 min at 4° C. The supernatants were immunoprecipitated using anti-EpCAM antibodies. HRP-conjugated secondary antibodies (Jackson Immuno Research Labs, West Grove, Pa.) were used and the signals were developed using enhanced chemiluminescence reagents (ECL) (Thermo Scientific, Rockford, Ill.).

Apoptosis Assays. Cells were separately seeded and treated with 0-20 µg/ml mAbs for 6 h. Apoptotic cells were detected by Annexin V-FITC and PI and analyzed by a flow cytometer (BD imnmmunocytometry systems, San Jose, Calif.). Early apoptosis was measured with the Annexin V-FITC Apoptosis Detection kit II (BD Pharmingen, La Jolla, Calif.). Apoptotic nuclei were detected with propidium iodide (PI) staining.

Animal Model for Analysis of Antitumor Efficacy. SCID mice bearing SAS-derived oral cancer xenografts (~75 mm$^3$) were intravenously injected in the tail vein with EpAb2-6 or equivalent volumes of PBS. Treatments were administered through tail vein injection, 10 mg/kg twice a week, for 4 consecutive weeks, with a total dose of 80 mg/kg. Tumors were measured by calipers twice weekly, and mice were observed routinely for weight loss as a symptom of drug toxicity. The tumor volumes were calculated as length×(width)$^2$×0.52. For combination therapy tumor model, SCID mice bearing HCT116-derived colon cancer xenografts (~50 mm$^3$) were divided into four groups based on the different treatment regimens (EpAb2-6, IFL, EpAb2-6 plus IFL, and PBS control). For the groups receiving EpAb2-6 only, mice were administrated with the EpAb2-6 monotherapy at a dose of 20 mg/kg through tail-vein by intravenously (i.v.) injection twice a week for 4 weeks (Weekly×4). For the groups receiving IFL only, IFL (5-FU of 25 mg/kg+leucovorin of 10 mg/kg+irinotecan of 10 mg/kg) were also administrated by intravenously (i.v.) injection twice a week for 4 weekly (Weekly×4). For combination treatment groups, EpAb2-6 was administered 24 h before IFL; both EpAb2-6 and IFL were given at the same dosage cycle as the other two groups. The procedures for EpAb2-6 combination IFL were modified from a previous report (Azrak R G et al. (2004) "Therapeutic synergy between irinotecan and 5-fluorouracil against human tumor xenografts" Clin Cancer Res. 10, 1121-9; Kim et al. (2010) "Dendritic cell vaccine in addition to FOLFIRI regimen improve antitumor effects through the inhibition of immunosuppressive cells in murine colorectal cancer model" Vaccine 28, 7787-7796).

Cloning and CDR Sequencing of Anti-EpCAM Antibodies. Total RNA was extracted from hybridoma cells using the TRIzol reagent (INVITROGEN®), and mRNA was isolated with the NucleoTrap mRNA Mini Kit (Macherey-Nagel GmbH & Co. KG.). Purified mRNA was reverse transcribed using oligo (dT) as a primer in a ThermoScript RT-PCR system (INVITROGEN®). The variable heavy- and light-chain domains ($V_H$ and $V_L$) were amplified from the cDNA product by PCR with a variety of primer sets. The PCR products were cloned using the TA kit (Promega, Madison, Wis.), and the $V_H$ and $V_L$ sequences were determined by DNA sequencing. Software Vector NTI (InforMax) was used for sequences analysis. From these sequences, the framework regions (FR) and complementarity-determining regions (CDR) were analyzed through comparison with those found in the Kabat database and with alignment to ImMunoGeneTics database (Lefranc et al. (2009) "IMGT, the international ImMunoGeneTics information system" Nucleic Acids Res. 37, D1006-12).

Construction and Expression of Humanized EpAb2-6. Humanized EpAb2-6 $V_H$ consisted of the modified FR1 to FR4 from the accession DI164282 gene, and the CDR1 to CDR3 of the EpAb2-6 Vii, respectively. The humanized EpAb2-6 $V_L$, CDRs consisted of the modified FRs from the accession GM882764 gene and the CDRs of the EpAb2-6 $V_L$. The resulting $V_H$ was cloned into modified expression vector pcDNA3.1 (INVITROGEN®) with a signal peptide and human IgG1 constant region. The $V_L$ was cloned into modified expression vector pSecTag (INVITROGEN®). The $V_H$ and $V_L$ plasmids were cotransfected into CHO-K1 cells and selected by G 418 and puromycin for 2-3 weeks. Transformed cells were limit diluted in 96-well plates. After two weeks, stable clones produced humanized antibody in the McCoy's 5A medium (SIGMA-ALDRICH) and were identified by ELISA. Humanized antibodies were produced by CELLine AD 1000 (INTEGRA Biosciences, Switzerland), according to manufacturer's recommendations.

Phage Display Biopanning. The phage display biopanning procedures were performed according to previous reports (Wu, et al., 2003; Liu, et al., 2011). Briefly, an ELISA plate was coated with mAbs at 100 µg/ml. Samples of 100 µg/ml mAb were then added to wells and incubated at 4° C. for 6 h. After washing and blocking, the phage-displayed peptide library (New England BioLabs, Inc.) was diluted to 4×10$^{10}$ pfu of phage and incubated for 50 mins at RT. After washing, bound phage was eluted with 100 ml of 0.2 M glycine/HCl (pH 2.2) and neutralized with 15 ml of 1 M Tris/HCl (pH 9.1). The eluted phage was amplified in ER2738 (New England Biolabs, Inc. MA, USA) for subsequent rounds of selection. The phage was titrated on LB/IPTG/X-Gal plates. The biopanning protocol for the second and third rounds was identical to the first round except for the addition of 2×10$^{11}$ pfu of amplified phage for biopanning.

Identification of EpAb2-6 Epitopes by EpCAM Mutants. We used the recombinant expression plasmid pcDNA™rM3.1/V5-His to generate EpCAM mutants. Various EpCAM mutants were generated by site-directed mutagenesis derived from pcDNA™3.1/V5-His as a template. PCR was performed using pfu ultra DNA polymerase (MERCK) and all mutant constructs were confirmed by sequencing. HEK293 cells at 80%-90% confluency in 6-well plates were transfected with plasmids of various EpCAMs. After two days transfection, the cells were washed with PBS. Cells were extracted with RIPA buffer, supplemented with a protease inhibitor mixture tablet and spun at 20,000 g for 30 min at 4° C. The wild-type and mutated recombinant protein were stained by incubating with 1 μg/ml primary antibody (EpAb2-6 or EpAb3-5), followed by HRP-conjugated secondary antibodies (Jackson Immuno Research Labs, West Grove, Pa.). The signals were developed using enhanced chemiluminescence reagents (ECL) (Thermo Scientific, Rockford, Ill.).

Surface Plasmon Resonance. The affinity of murine and humanized antibodies was performed by surface plasmon resonance (BIAcore T100, Biacore, Inc). EpCAM antigen was immobilized on a Series S Sensor Chip CM5 (Biacore, Inc) and injected at a flow rate of 10 μl/min. The mAbs were diluted in HBS-EP$^+$ buffer (Biacore, Inc) and injected at a flow rate of 50 μl/min for 1.5 min, and were allowed to dissociate over 5 min. Regeneration of the surface was achieved with an injection of 10 mM glycine HCl, 0.2 M NaCl (pH2.5) before each mAb injection. The data were analyzed by the BIAevaluation software with a global fit 1:1 binding model.

RNA Extraction and Quantitative Real-Time RT-PCR. Total RNAs were prepared from the cell lines using ULTRASPEC RNA isolation reagent (Biotecx Laboratories, Houston, Tex.). cDNAs were reverse-transcribed using Super-Script III RNaseH-reverse transcriptase (INVITROGEN®, Carlsbad, Calif.) according to the manufacturer's instructions. The forward and reverse primers used for cloning, Quantitative RT-PCR are listed in Table 1. Quantitative RT-PCR was performed by using the LightCycler480 System (Roche Applied Science). The gene expression level of each sample was normalized to the expression level of GAPDH in the same sample. The reactions were performed in triplicate, and S.D. values were calculated.

TABLE 1

| Assay | Gene | Sequence (5'→3') |
|---|---|---|
| Q-RT-PCR primers | EpCAM | F: CTCCACGTGCTGGTGTGT (SEQ ID NO: 26)<br>R: TGTTTTAGTTCAATGATGATCCAGTA (SEQ ID NO: 27) |
| | c-Myc | F: AAACACAAACTTGAACAGCTAC (SEQ ID NO: 28)<br>R: ATTTGAGGCAGTTTACATTATGG (SEQ ID NO: 29) |
| | Nanog | F: ATGCCTCACACGGAGACTGT (SEQ ID NO: 30)<br>R: AGGGCTGTCCTGAATAAGCA (SEQ ID NO: 31) |
| | Sox2 | F: TATTTGAATCAGTCTGCCGAG (SEQ ID NO: 32)<br>R: ATGTACCTGTTATAAGGATGATATTAGT (SEQ ID NO: 33) |
| | Oct4 | F: AGCAAAACCCGGAGGAGT (SEQ ID NO: 34)<br>R: CCACATCGGCCTGTGTATATC (SEQ ID NO: 35) |
| | E-cadherin | F: GGAACTATGAAAAGTGGGCTTG (SEQ ID NO: 36)<br>R: AAATTGCCAGGCTCAATGAC (SEQ ID NO: 37) |
| | Vimentin | F: GTTTCCCCTAAACCGCTAGG (SEQ ID NO: 38)<br>R: AGCGAGAGTGGCAGAGGA (SEQ ID NO: 39) |
| | Snail | F: CTTCGGCTCCAGGAGAGTC (SEQ ID NO 40)<br>R: TTCCCACTGTCCTCATCTGAC (SEQ ID NO: 41) |
| | Slug | F: TGGTTGCTTCAAGGACACAT (SEQ ID NO: 42)<br>R: GTTGCAGTGAGGGCAAGAA (SEQ ID NO: 43) |
| | GAPDH | F: CTTCACCACCATGGAGGAGGC (SEQ ID NO: 44)<br>R: GGCATGGACTGTGGTCATGAG (SEQ ID NO: 45) |
| | 18s rRNA | F: GCAATTATTCCCCATGAACG (SEQ ID NO: 46)<br>R: GGGACTTAATCAACGCAAGC (SEQ ID NO: 47) |
| ChIP primers | c-Myc | F: GCCTGCGATGATTTATACTCAC (SEQ ID NO: 48)<br>R: AAACAGAGTAAGAGAGCCG (SEQ ID NO: 49) |
| | Nanog | F: TCTTCAGGTTCTGTTGCTCG (SEQ ID NO: 50)<br>R: GTTAATCCCGTCTACCAGTCTC (SEQ ID NO: 51) |
| | Sox2 | F: GGATAACATTGTACTGGGAAGGGACA (SEQ ID NO: 52)<br>R: CAAAGTTTCTTTTATTCGTATGTGTGAGCA (SEQ ID NO: 53) |

TABLE 1-continued

| Assay | Gene | Sequence (5'→3') |
|---|---|---|
| | Oct4 | F: CGCCTCGAGTGGGGAACCTGGAGGATGGCAAG (SEQ ID NO: 54)<br>R: TATAAGCTTGGGGAAGGAAGGCGCCCCAAG (SEQ ID NO: 55) |
| | GAPDH | F: TCCAAGCGTGTAAGGGT (SEQ ID NO: 56)<br>R: GAAGGGACTGAGATTGGC (SEQ ID NO: 57) |
| Cloning primers | EpEX | F: TATAAGCTTACCATGGCGCCCCCGC (SEQ ID NO: 58)<br>R: CGCCTCGAGAATAACCAGCACAA (SEQ ID NO: 59) |
| | EpCAM | F: GATAAGCTTATGGCGCCCCCGCAGGTC (SEQ ID NO: 60)<br>R: GATCTCGAGTGCATTGAGTTCCCTATGCATCTCACC (SEQ ID NO: 61) |

Spheroid Assay. For spheroid formation, culture cells were disassociated into single cells. $5\times10^3$ cells were seeded at an ultra-low 6-well plate (CORNING™ for 6 days and were maintained in DMEM/F12 supplemented with B27 (INVITROGEN®), EGF (10 ng/ml) and FGF (25 ng/ml) twice a week. The spheres were counted under a microscope. For serum-induced differentiation assay, tumorspheres were cultured in matrigel-coated plate supplemented with DMEM containing 10% FBS for 7 days to induce the differentiation process.

Plasmid Constructions. Full-length human EpCAM was cloned into pcDNA3.1 vector tagged with v5 and 6×His. The pEpEX$_{291}$ (composed of the extracellular and transmembrane domain of EpCAM) and pEpICD plasmids were subconstructed from pcDNA3.1-EpCAM. Luciferase reporter activities were constructed by inserting the PCR fragments of c-MYC (−1224/+47 related to transcriptional start site), OCT4 (−2616/+1), and NANOG (−1590/+250) into pGL4.1 plasmid (Promega). Lentivirus encoding small hairpin RNA of EpCAM (pLKO-shEpCAM) and the control plasmid pLKO-ASI were obtained from RNAi core facility (Academia Sinica).

Lentivirus Infection. HEK293T packaging cells were co-transfected with packaging plasmid (pCMV-ΔR8.91), envelope (pMDG), and hairpin pLKO-RNAi vectors by PolyJET transfection kit (SignaGen Laboratories). After 48 h post-transfection, virus-containing supernatant were collected, mixed with fresh medium containing polybrene (8 µg/ml), and incubated with target cells for a further 48 h infection. The transduced cells were selected with puromycin (4 µg/ml) for 4 day.

Luciferase Reporter Assay. Cells were seeded in a plate and co-transfected with pcDNA3.1, EpCAM, EpICD, or EpEX-expressing vectors (400 ng) and pGL4-Oct4-Luc, Nanog-Luc, Sox2-Luc, or c-Myc-Luc-expressing plasmid (100 ng) by PolyJET for 24 h. Promoter activities were measured by the Dul-Glo Luciferase kit (Promega), and the transfected efficiency was normalized by co-transfection with pRL-TK (20 ng) as an internal control.

Colony Formation and Invasion Assay. For colony formation assay, cells were seeded at a density of $5\times10^3$ in 6-well plate for 10 day, followed by fixing and staining with crystal violet. For invasion assay, cells ($1\times10^5$) were seeded at a transwell insert (8-µm polycarbonate Nucleopore filters, Corning) coated with Matrigel (BD Biosciences) at room temperature for 30 min to form a genuine reconstituted basement membrane. After 24 h incubation, cells were fixed with methanol for 10 min, and non-invaded cells were then removed by cotton swap. The invaded cells were observed by staining with DAPI, imaged under an inverted fluorescent microscopy (Zeiss), and quantified by ImageJ software.

Statistical Analysis. All data were derived from at least three-independent experiments. Values are expressed as mean±SD. The significance of difference from the respective control for each experimental test condition was calculated using Student's t-test, unless specified otherwise. * p value <0.05,  p value <0.01 or * p value <0.001 was regarded as a significant difference. Survival analysis was performed by log-rank test. Correlation coefficient was assayed by Spearman's analysis.

Results

Generation and Characterization of mAbs that Recognized Oral Cancer Cells

For the generation of monoclonal antibodies against oral cancer, we injected SAS cells into the BALB/cJ mice. More than 8,000 hybridoma clones were screened, and twelve clones exhibiting higher reactivities against SAS cells were selected (FIG. 15). Cellular ELISA and Western blot analyses showed that OCAb9-1 specifically recognized several human cancer cells but not normal cells, such as NNM or HUVEC cells (FIG. 1). Further experiments using various human cancer tissue arrays also showed that OCAb9-1 was able to specifically recognize human cancer tissues of different origins, but not normal tissues (FIG. 1C).

Figure 2:
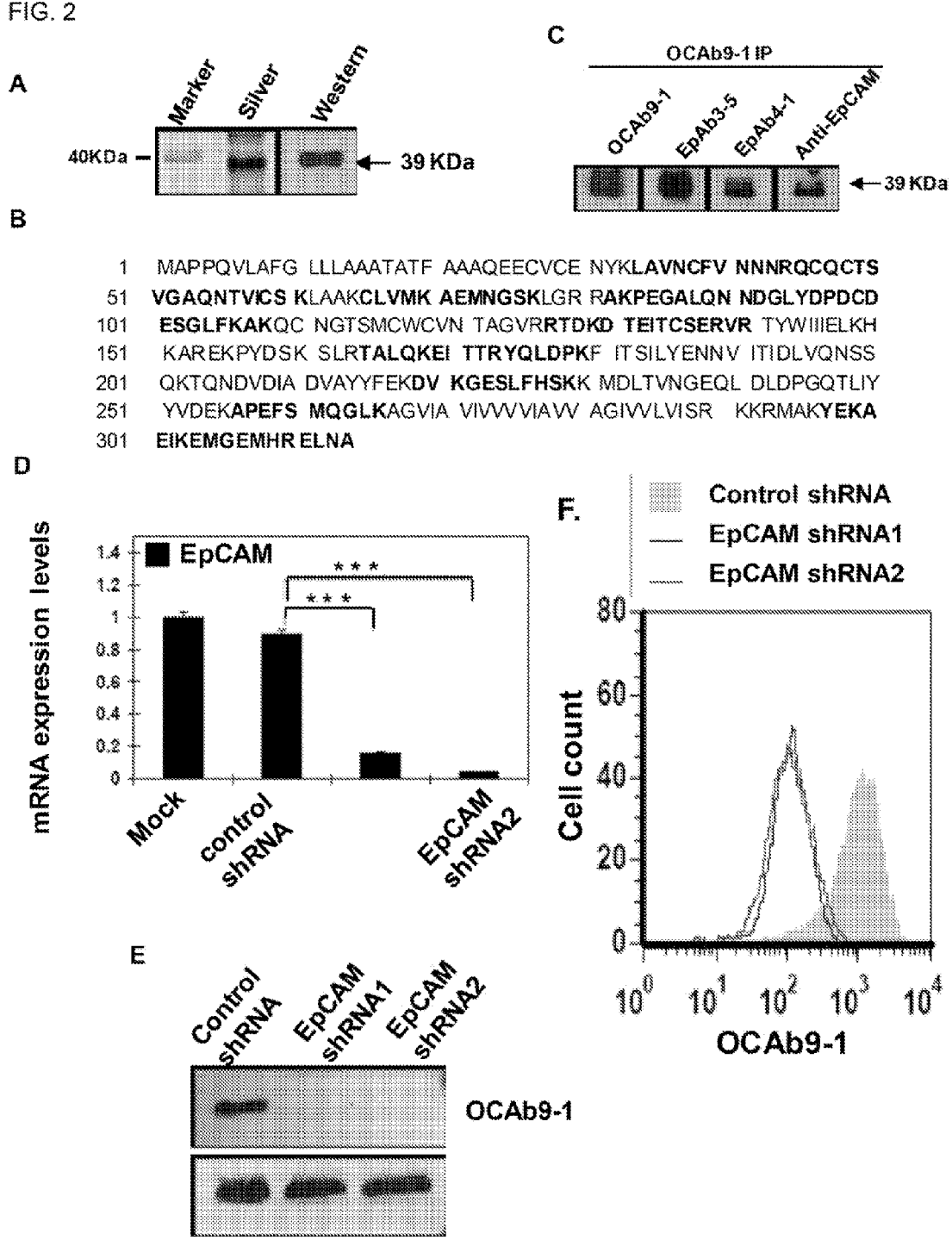
FIG. 2 shows Identification of OCAb9-1-targeted Protein. (A) Purification of OCAb9-1-targeted protein by immunoaffinity chromatography. Lane 1, molecular weight marker; lane 2, purified proteins from OCAb9-1-conjugated affinity column; and lane 3, Western blot analysis of purified proteins from OCAb9-1-conjugated affinity column. A 39 kDa protein (star denoted) was purified and subjected to LC/MS/MS analyses. (B) Swiss-Prot database confirms the target protein of OCAb9-1. Full-length of human TACSTD1 (EpCAM) contained 314 amino acid polypeptides (SEQ ID No: ). Highlighted sequences indicated the hit peptide by LC/MS/MS. (C). SAS lysates with immunoprecipitated with OCAb9-1 antibody and subsequent blotted with rabbit anti-EpCAM mAb (1144-1) and EpAb3-5, EpAb4-1 antibodies. (D) After the transfection of two EpCAM shRNAs plasmids (shEpCAM1 and shEpCAM2) separately into the SAS cell lines, the total RNAs of each line were extracted and examined by QRT-PCR analysis. Both shEpCAM1 and shEpCAM2 had a clear suppressive effect on EpCAM mRNA expression in the transfected SAS lines. Samples of mixed clone cells were measured, each point representing the mean value±SEM (n=3). ***, P<0.001. (E) Western blot and (F) flow cytometry analyses were performed to evaluate anti-OCAb9-1 mAb binding to control and EpCAM knockdown SAS cells.

For target molecule identification, the SAS cell lysates were prepared and purified by OCAb9-1-conjugated immunoaffinity chromatography. Silver stain and Western blotting demonstrated that OCAb9-1 recognized a target protein with a molecular weight of 39 kDa (FIG. 2A). Protein identity was analyzed by LC-MS/MS, we found the target protein of OCAb9-1 to be a human EpCAM (FIG. 2B). The specificity of OCAb9-1 to EpCAM was confirmed by conducting immunoprecipitation and Western blotting in parallel with commercial anti-EpCAM antibody 1144-1 (Santa Cruz Biotech; Epitomics respectively) (FIG. 2C). Western blotting (FIG. 2E) and FASC (FIG. 2F) with OCAb9-1 showed a dramatic decrease in signal after the knockdown of EpCAM by shRNA (FIG. 2D), confirming that OCAb9-1 specifically recognized EpCAM (FIG. 2).

Figure 3:
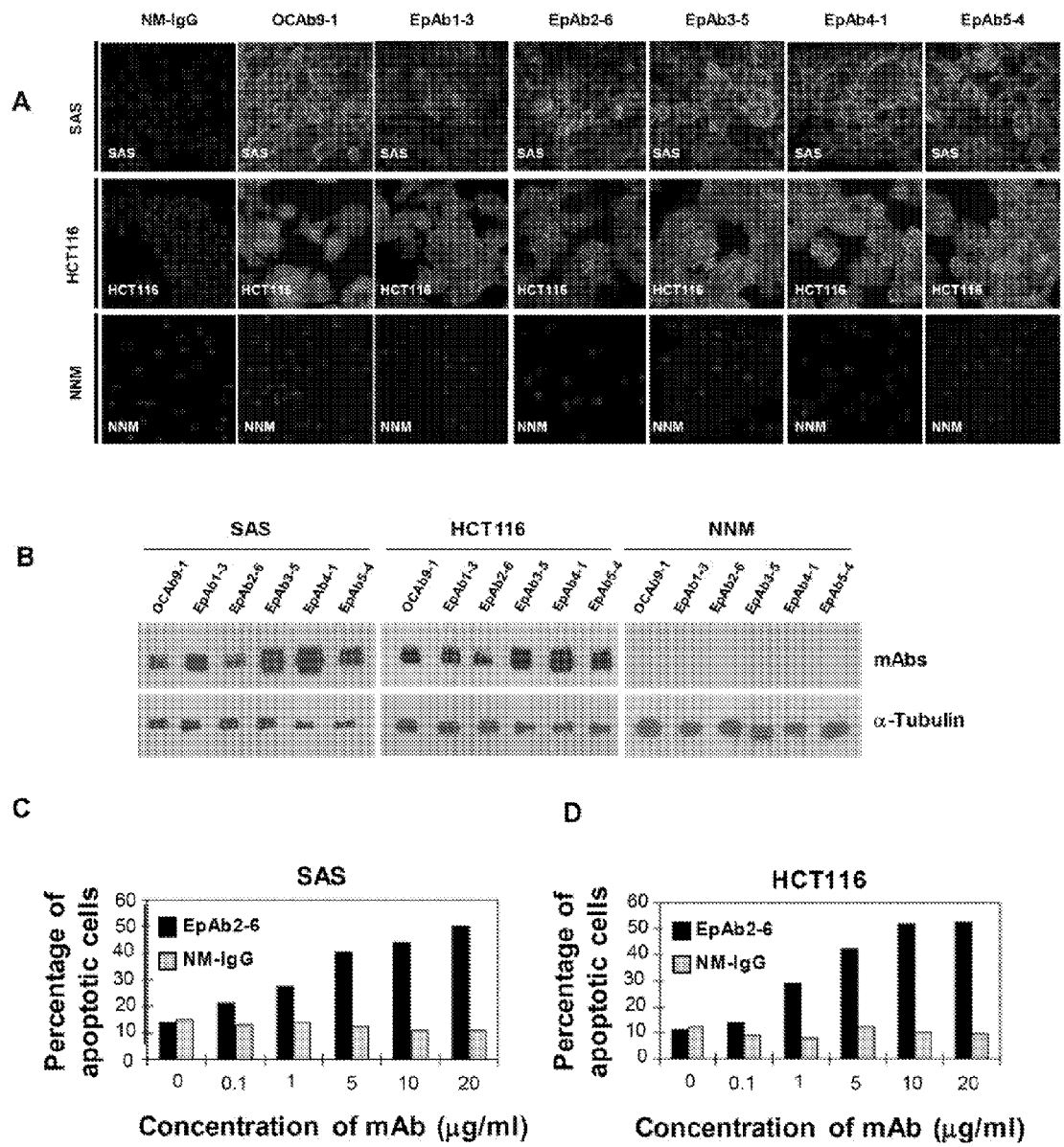
FIG. 3 shows Characterization of anti-EpCAM mAbs. OCAb9-1 and EpAb mAbs recognized human cancer cell lines. SAS, HCT116, and NNM cells were incubated with OCAb9-1 and EpAb mAbs. Binding activities of anti-EpCAM mAbs were measured by flow cytometry. Immunofluorescence staining (A) and Western blotting (B). SAS (C) and HCT116 cells (D) were treated with EpAb2-6 (0-20 µg/ml) for 6 h, and cells death was measured by flow cytometry with Annexin V-FITC and PI double staining. Annexin V-FITC was used to determine the percentage of cells within the population that are actively undergoing apoptosis at an early stage (6 hours). Propidium iodide (PI) was used to distinguish viable from nonviable cells.

OCAb9-1 cannot induce cancer cell apoptosis. To develop therapeutic antibodies, we purified EpCAM protein from SAS cells and newly generated five mAbs that recognized EpCAM (FIG. 16). These mAbs had a strong detection signal for cancer cell lines (SAS, NPC039, HCT116 and SKOV3) but they showed no binding affinity to normal cell lines (HUVEC and NNM), as shown by cellular ELISA, Western blot and FACS analysis (FIG. 16). These mAbs were demonstrated to have extremely high cell surface binding activity for SAS and HCT116 cells, but they did not react to NNM cells, as shown by FACS (data not shown), immunofluorescent analysis (FIG. 3A) and Western blotting (FIG. 3B). Three complementarity-determining regions (CDRs) in the heavy and light chains of these mAbs are shown in FIG. 17. All of these mAbs have very high affinity to EpCAM and their kinetic constants range from $10^{-9} \sim 10^{-13}$ (FIG. 18). Notably, one of five newly generated mAbs, EpAb2-6, could induce cancer cell apoptosis using SAS and HCT116 cell lines (FIGS. 3C-D).

Inhibition of Cancer Cell Growth In Vitro and In Vivo

Figure 4:
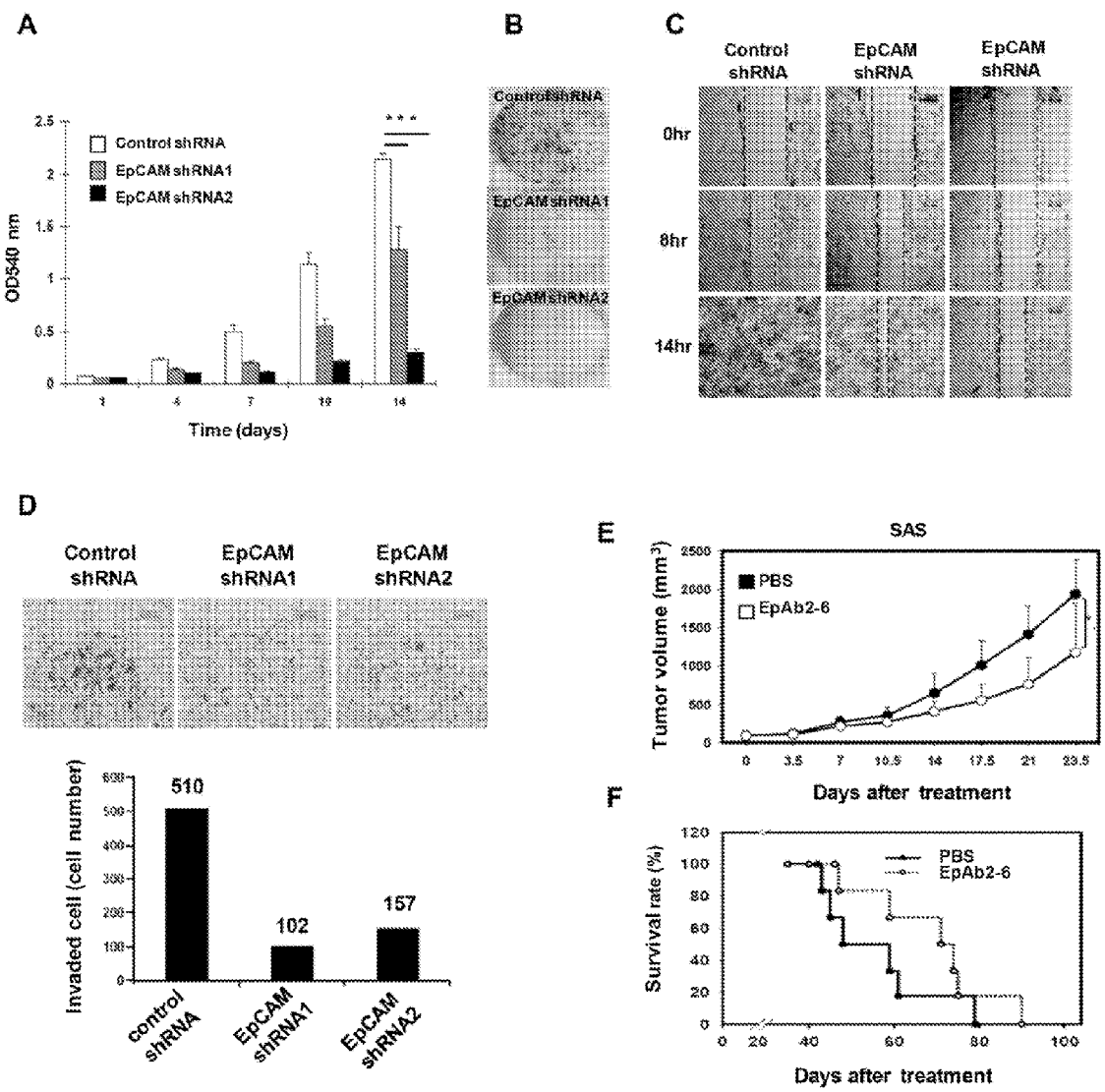
FIG. 4 shows inhibition of Cancer Cell Growth in vitro and in vivo by EpCAM shRNA and EpAb2-6. Knockdown of EpCAM expression in SAS cells by EpCAM shRNA (shEpCAM). LKO shRNA vector alone (control shRNA) was used as a control. (A) Down-regulation of EpCAM inhibited cell proliferation in SAS cells. Cell viability was performed by MTT assay. , p<0.01, *, p<0.001. (B-D) Suppression of EpCAM inhibits colony formation (B) migration (C) and invasion (D) of tumor cells in vitro. (E) Suppression of EpCAM reduces tumor growth in vivo. (E) Suppression of EpCAM reduces tumor growth in vivo. NOD/SCID mice bearing SAS-derived tumor xenografts were treated with EpAb2-6 mAb (10 mg/kg) or PBS, and tumor volumes were measured (n=6) (data were presented as mean±SD, and p value was analyzed by I-test). Error bars denote ±SD. *, P<0.05. (F) A Kaplan-Meier survival curve showed longer lifespan of mice treated with EpAb2-6 and PBS (n=6 in each group).
Figure 5A:
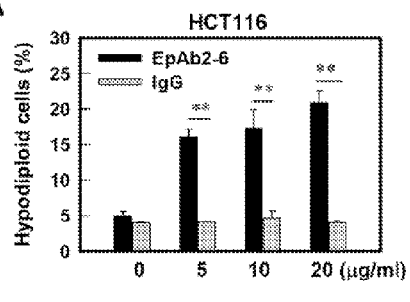
FIGS. 5A-D show EpAb2-6 reduces Tumorsphere Formation. EpAb2-6 increases hypodiploid DNA content in HCT116 (A) and tumorsphere (HCT116 sphere) (B) by flow cytometry with Propidium iodide (PI) staining. EpAb2-6 reduces tumorsphere formation (C). HCT116 sphere cells were treated with EpAb2-6 for 6 days, and numbers of tumorspheres were counted (D).
Figure 5B:
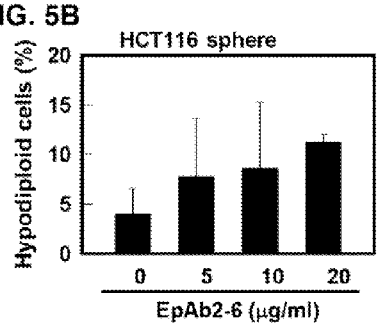
Figure 5C:
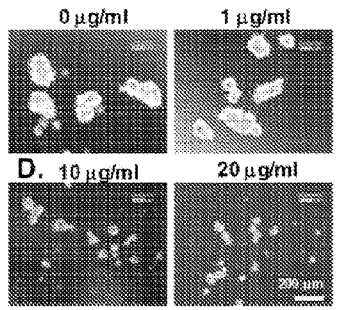
Figure 5D:
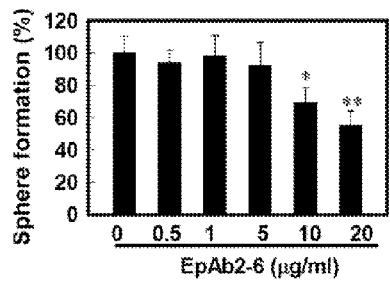

To evaluate the functional role of EpCAM in tumorigenesis, the gene expression was knocked down by EpCAM shRNA in SAS cells. The growth rate (FIG. 4A), colony formation (FIG. 4B), migration (FIG. 4C) and invasion ability (FIG. 4D) were significantly reduced when EpCAM was knocked down. Since EpCAM knockdown affected cancer cell growth and induced cancer cell apoptosis in vitro, we investigated whether EpAb2-6 could be used to directly inhibit tumor growth in vivo. Oral cancer xenografts were established and treated with either EpAb2-6 or control PBS. The volume of the tumors treated with EpAb2-6 became smaller than those of the two controls. The tumors of the control PBS group was found to be 1.5-fold larger than those of the EpAb2-6 group, respectively (n=6: *, p<0.05; FIG. 4E). To further characterize therapeutic efficacy of antibody, we compared the survival rates of tumor-bearing mice after treatment with EpAb2-6 and PBS. The median overall survival of tumor-bearing mice after treatment with EpAb2-6 and PBS was 71 and 48 days, respectively (FIG. 4F). Treatment of EpAb2-6 suppressed tumorsphere formation effectively (FIG. 5C) and induced hypodiploid DNA content in both tumor and tumorsphere cells (FIGS. 5A and 5B). These experiments demonstrate that targeting EpCAM by EpAb2-6 inhibited tumorsphere formation and tumor growth, while prolonged the lifespan of tumor-bearing mice.

Combination of EpAb2-6 and IFL in Human Colon Carcinoma Xenograft

Figure 6:
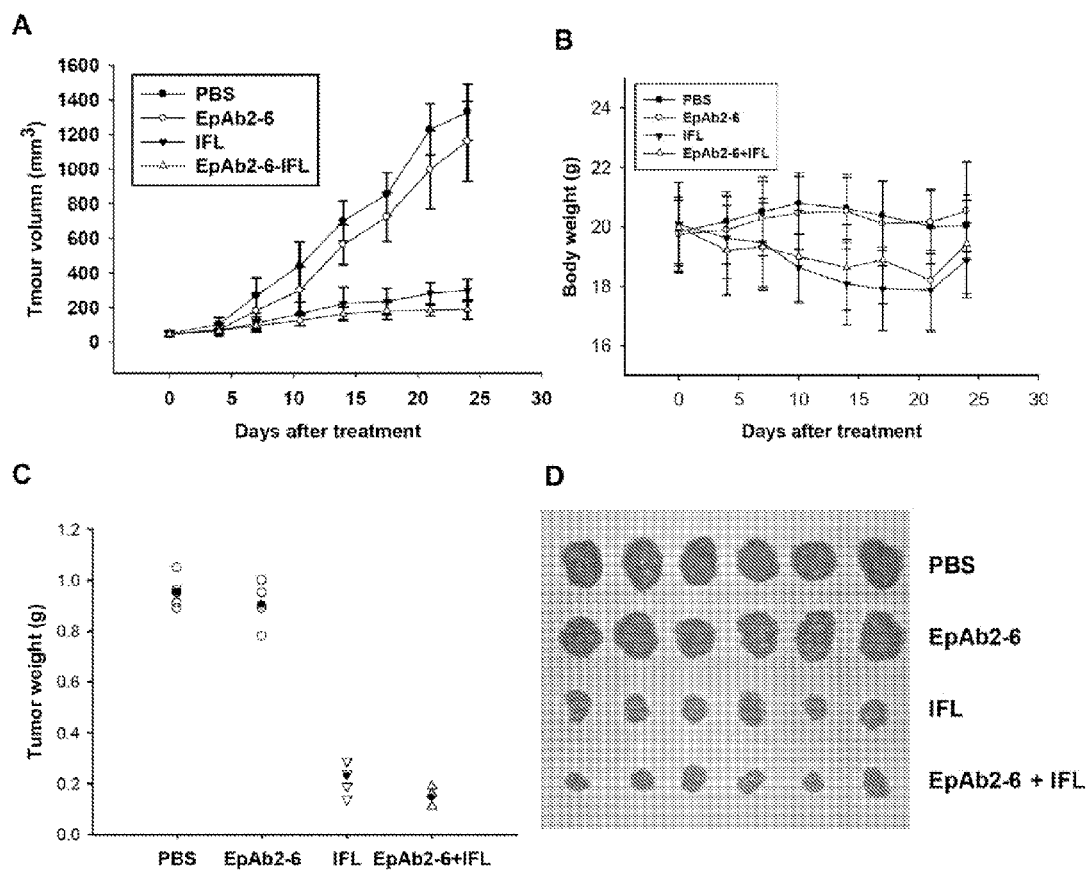
FIG. 6 shows the effect of EpAb2-6 alone or EpAb2-6 in Combination with IFL Against HCT116 Tumor-bearing Mice. (A) Mice bearing HCT116-derived colon cancer were administered EpAb2-6, IFL, EpAb2-6 in combination with IFL, and PBS. The tumor sizes in each group were determined (n=6 in each group). Points, mean; bars, SD. (B) Body weight of each group. (C) At the end of the treatment, tumor weight was measured. (D) Representative image of analysis depicted in (C). *, p<0.05 denotes a significant difference.

To evaluate the therapeutic efficacy of EpAb2-6 in combination with IFL, we injected HCT116 ($3\times10^6$ cells) into NOD/SCID mice. NOD/SCID mice bearing HCT 16 xenografts (~50 mm$^3$) were injected intravenously with a combination of EpAb2-6 (20 mg/kg) and IFL (5-FU of 25 mg/kg+leucovorin of 10 mg/kg+irinotecan of 10 mg/kg) twice a week for a total of eight injections. The tumors in mice with treatment using combination of EpAb2-6 and IFL were found to be smaller than that in mice with treatment using IFL alone (*, P<0.05) (FIG. 6A). The tumor size of the IFL group gradually increased to 1.6-fold that of the EpAb2-6+IFL by day 25. The EpAb2-6+IFL and IFL groups did not have significant changes in body weight during treatment period (FIG. 6B). By the end of the treatment, the final average tumor weight in mice treated with IFL was 0.23 g, compared to 0.146 g in mice treated with EpAb2-6+IFL, and 0.952 g in mice injected with PBS buffer (FIGS. 6C and D).

Development of Humanized EpAb2-6 (hEpAb2-6)

EpAb2-6 possessed the high affinity and potent activity for induction of cancer cell apoptosis, which suggested its potential as a therapeutic antibody. To develop humanized mAbs, we sequenced $V_H$ and $V_L$ segment of the EpAb2-6 mAbs from hybridoma cell lines (FIG. 17). The CDRs of EpAb2-6 were grafted onto human IgG1 backbone to create humanized EpAb2-6 (hEpAb2-6) (FIG. 7A). The hEpAb2-6 was expressed in CHO-K1 cells and purified from culture supernatants. The hEpAb2-6 that maintained the specificity of murine EpAb2-6 (mEpAb2-6) recognized both SAS and HCT116 cancer cells but not CCD-1112Sk normal cells. Cellular ELISA and Western blotting further demonstrated highly binding activities of hEpAb2-6 (FIGS. 7B-D). The affinity of EpAb2-6 and hEpAb2-6 for EpCAM was analyzed by surface plasmon resonance and was determined as 0.3491 nM and 0.6773 nM, respectively (FIG. 18). Furthermore, in vitro studies using SAS and HCT116 cell lines found that hEpAb2-6 induced cancer cell apoptosis (FIGS. 7E-F). The results reveal that humanized EpAb2-6 possesses high binding affinity to EpCAM, which suggested its potential applications in cancer therapy as therapeutic antibody, or tumor-targeted drug delivery, and imaging.

Identification of EpAb2-6-Specific B Cell Epitopes.

Figure 8A:
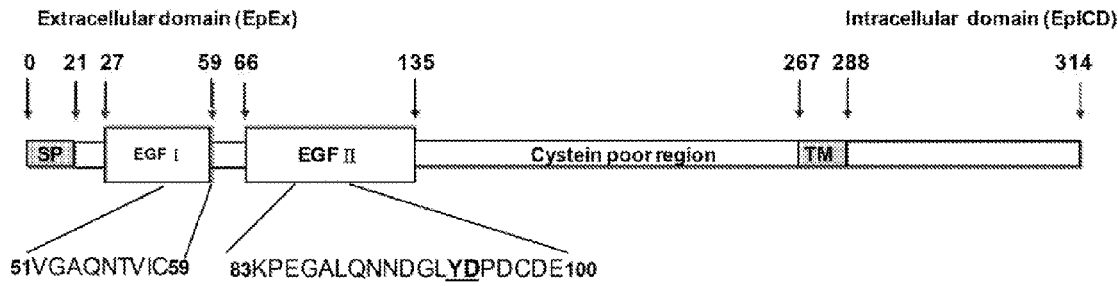
FIGS. 8A-B show identification of EpAb2-6-specific B Cell Epitopes. (A) We constructed various EpCAM mutations by changing the amino acid on the wild-type of EGF-I domain SEQ ID No: 62(Q54A/N55A) or EGF-II domain SEQ ID NO: 63 (Q89A/N90A, D92A/G93A, L94A/Y95A, L94A, Y95A or D96A). (B) Various EpCAM mutants were expressed in HEK293 cells. After extracting the cell protein, Western Blotting was used to test the reactivity of EpAb2-6 and EpAb3-5 antibodies toward various EpCAM mutants. Substitutions of Y95 and D96 led to a significant loss of binding activity of EpAb2-6 mAbs, which reflected the sequence on EGF-II as shown in (A).
Figure 8B:
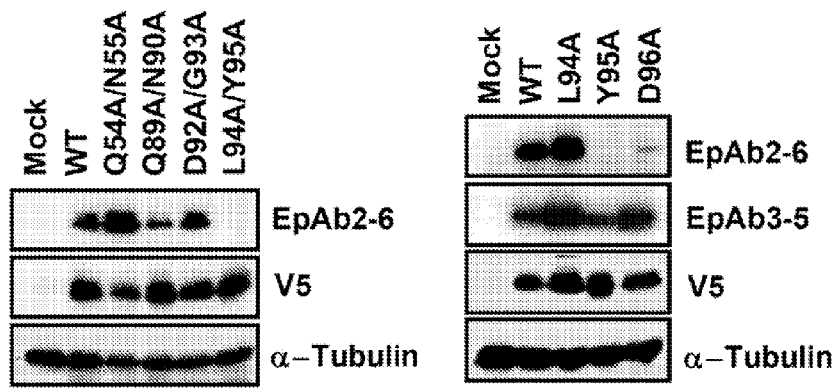

Eighteen immunopositive phage clones (PC-26, -11, -29, -3, -4, -18, -12, -1, -19, -27, -35, -21, -37, -20, -2, -7, -8 or -44) that were highly reactive with EpAb2-6-specific antibody and less reactive with antibodies in normal mouse IgG were amplified, and phage DNA was isolated for sequencing. Inserted nucleotides of selected phage clones were sequenced, and all clones were found to contain 36 nt (translated into 12 aa residue, SEQ ID Nos: 64-72, respectively) (FIG. 19). Peptide sequences SEQ ID NOs: 64-73were aligned by using MacDNASIS software to analyze epitopes and binding motifs of EpAb2-6 antibody. The cDNA encoding the sequence covering the first EGF-like repeat (aa 27-59) of human EpCAM (EGF-I) or second EGF-like repeat (aa 66-135) of human EpCAM (EGF-II) was amplified by PCR. Overlapping PCR and PCR-based site-directed mutagenesis were used to introduce mutation shown in FIGS. 8A-B into the wild-type of EGF-I or EGF-II domain. A Western blotting was used for testing the reactivity of EpAb2-6 or EpAb3-5 antibodies toward variant EpCAM mutants. The binding of each EpAb2-6 antibody to individual EpCAM mutant (FIG. 8B) was studied and compared to the binding to wild type EpCAM molecule. The amino acids mutations in positions Y95 or D96 on EGF-II domain cause markedly reduction in the relative binding activity, hence Y95 and D96 are considered "essential" residues for the antibody binding. FIG. 8 shows the sequences VGAQNTVIC (SEQ ID NO: 62) in the EGF-like domain I and KPEGALQNNDGLYDPDCDE (SEQ ID NO: 63) in the EGF-like domain II of EpCAM.

Elevation of EpCAM is Associated with Tumor-initiating Properties

Figure 9:
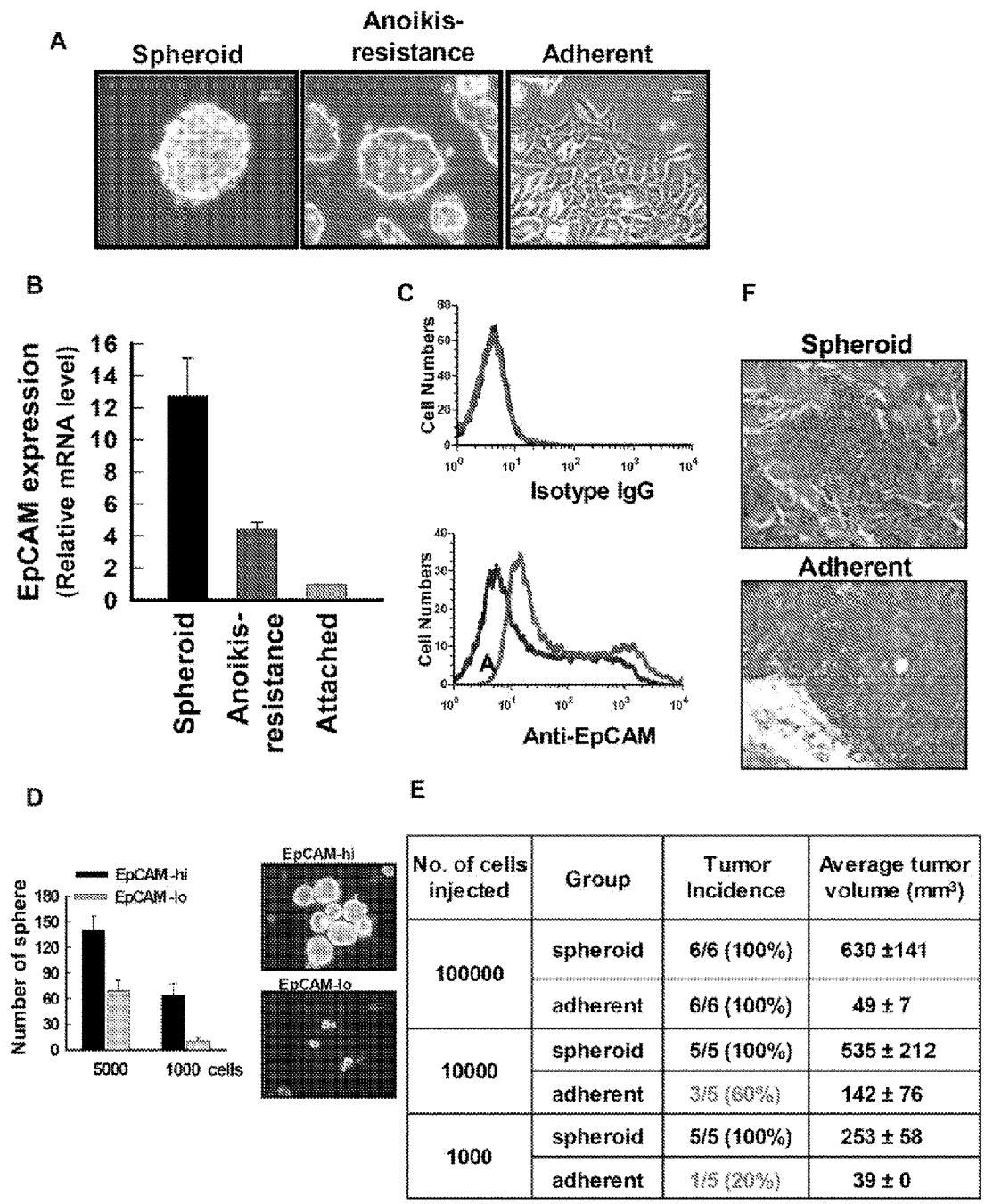
FIG. 9 shows elevation of EpCAM is Associated with Tumor-initiating and Self-renewal Ability of Aumor Cells. Elevation of EpCAM is determined in spheroid and anoikis-resistant tumor cells. (A) Bright field images of morphological alteration in spheroid, anoikis-resistance, and in adherent HCT116 cells. (B) Real-time qPCR (left) and flow cytometry (C) analyses of EpCAM expression in above cells are shown. (D) Spheroid formation from sorted EpCAM-high and -low expressed cells were counted in triplicate. Representative images of tumorsphere from EpCAM-high and -low cells are shown. (E) Evaluation of tumor-initiating capacity in spheroid and adherent HCT116 cells in mice. Tumor incidence and tumor volume were monitored for 35 days. (F) Histological analyses of H&E stained tumor sections (top: invasion front infiltrating in between the adjacent murine skeletal muscles, bottom: well-defined expansile tumor boundary rather than tissue infiltration is noted.

Tumor-initiating cells are endowed with the ability to be attached independently. Hence we selected HCT116 colon cancer cells in two kinds of anchorage-independent cultures, tumorsphere formation and anoikis-resistant selection (FIG. 9A). Interestingly, expression of EpCAM mRNA was elevated in both anoikis-resistance (4-folds) and spheroid (12-folds) cells, compared to that in adherent culture (FIG. 9B left). The enrichment of cell surface EpCAM was found to increase by four folds in spheroid-formation (FIG. 9C) and two folds in anoikis-resistance cells (data not shown), when compared to that in adherent cells via flow cytometric analysis. Similarly, expression of EpCAM was raised by 45% in sphere-forming hepatoma H-ep3B cells (98% enrichment) compared to that in adherent type cells (69% enrichment). This elevation was observed to have declined after reattachment of spheroid in the differentiated condition. CD133, a marker for TICs, was further confirmed to increase by 4 folds in sphere-forming Hep3B cells, but it decreased after differentiation (data not shown). Moreover, EpCAM-enriched subpopulation of HCT116 cells displayed dramatic sphere-forming ability (FIG. 9D). A comparison of tumorigenic potential between adherent and sphere-forming cells showed that sphere-derived HCT116 cells displayed superior tumor-initiating capabilities (FIG. 9E). We also found that spheroid-derived tumor xenografts exhibited both more aggressive self-renewal properties (FIG. 9F). This suggests that the elevated expression of EpCAM might be involved in tumor-initiating capability.

EpCAM Regulates Reprogramming Gene Expression and Tumor-initiating Ability

Figure 10:
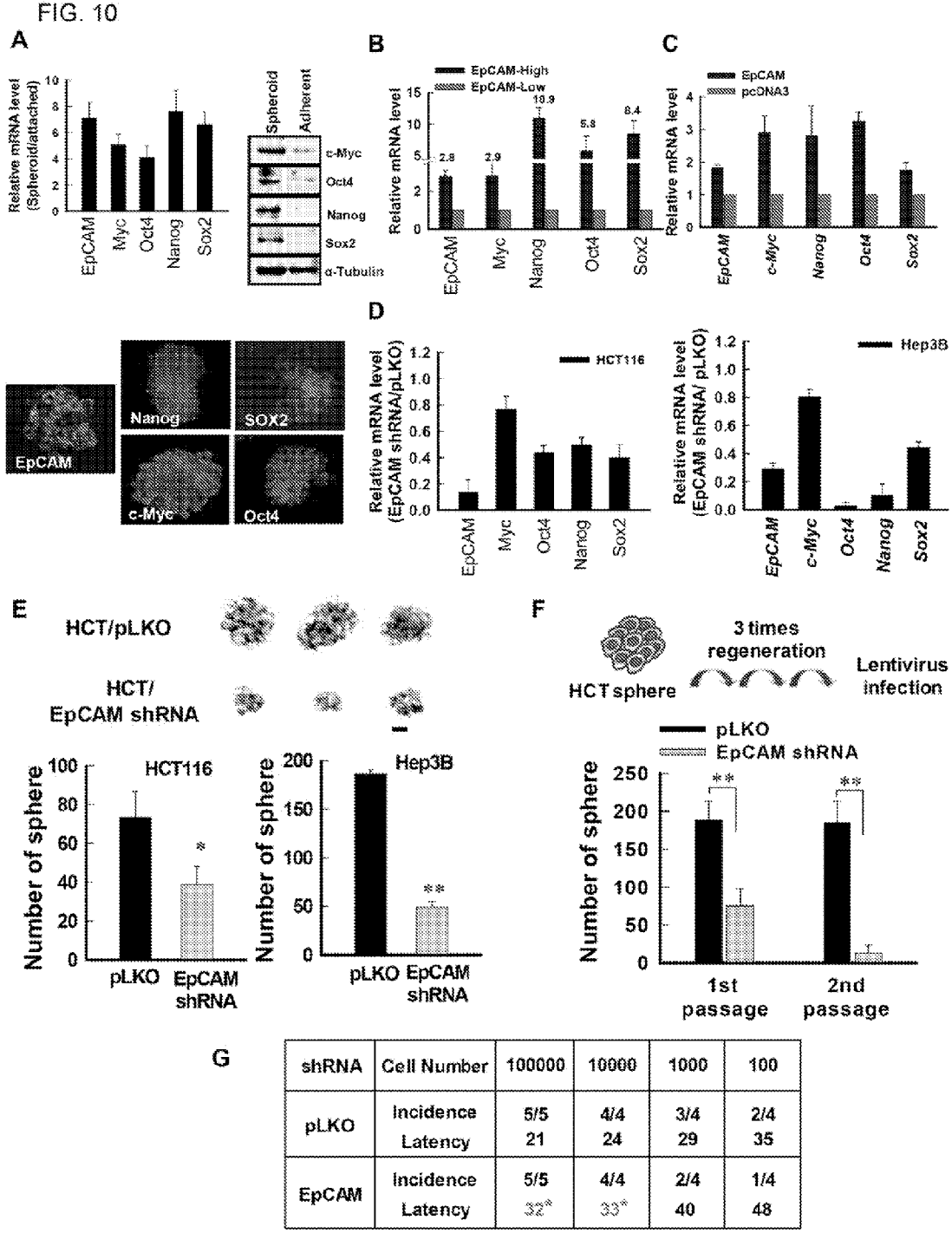
FIG. 10 shows EpCAM Up-regulates Reprogramming Genes (c-MYC, OCT4, NANOG, and SOX2) Expression and Self-renewal of Cancer Cells. (A) Increasing EpCAM and reprogramming genes expressions in spheroid tumor cells. Real-time qPCR (top left), Western blotting (top right), and immunofluorescence staining (bottom) analyses of the expressions of EpCAM, c-Myc, Oct4, Nanog, and Sox2 in spheroid and adherent HCT116 cells. (B) Real-time qPCR analysis of genes expression in EpCAM-high and -low expressed HCT116 cells. (C) Ectopic expression of EpCAM in HEK293 cells, and reprogramming gene expression were analyzed by real-time qPCR. (D) Real-time qPCR analysis of EpCAM, c-Myc, Oct4, Nanog, and Sox2 mRNA level in EpCAM knockdown Hep3B and HCT116 cells. (E) Suppression of EpCAM reduces tumorsphere formation in Hep3B and HCT116 cells. Bar=50 µm. (F) Knockdown of EpCAM in tumorsphere impacts self-renewal ability in vitro. Experimental procedure is shown in above. ** p<0.01 denotes a significant difference. (G) in vivo limiting dilution assay demonstrates that EpCAM knockdown in tumorsphere inhibits tumor-initiating capability. * p<0.01 was analyzed by log-rank test.

Quantitative PCR, Western blotting, and immunofluorescence analyses consistently showed that the expressions of both EpCAM and reprogramming genes (c-Myc, Oct4, Nanog, and Sox2) were concomitantly up-regulated in spheroid cells (FIG. 10A). Similar results were observed in EpCAM-enriched HCT116 cells (FIG. 10B). To investigate whether EpCAM can regulate reprogramming gene expression, we transfected EpCAM constitutive expression vector into HEK293 cells. Quantitative PCR analysis showed that overexpression of EpCAM induced increasing c-Myc, Oct4, Nanog, and Sox2 mRNA levels (FIG. 10C). In contrast, knockdown of EpCAM by lentivirus-mediated shRNA in both Hep3B and HCT116 cells abrogated EpCAM, c-Myc, Oct4, Nanog, and Sox2 mRNA expressions (FIG. 10D). Furthermore, silencing of EpCAM inhibited both number and size of Hep3B and HCT116 spheres, confirming the effect of EpCAM on tumorsphere-forming capacity (FIG. 10E). In order to further assess the importance of EpCAM on tumor cells self-renewal ability, HCT116 spheres were disassociated and regenerated three times, followed by silencing of EpCAM. Results showed that after EpCAM shRNA challenge, the regenerating ability of sphere was drastically decreased during the follow-up passage (FIG. 10F). Moreover, in vivo serial-diluted transplantation of HCT116 spheroid revealed that the knockdown of EpCAM in tumorsphere significantly hindered tumor-initiating potential and effectively retarded tumor latency (FIG. 10G). Collectively, these data indicated that EpCAM is essential in regulating reprogramming gene expression and maintaining self-renewal capacity.

EpCAM Regulates EMT Progression and Tumorigenesis

Epithelial-mesenchymal transition (EMT) has been shown to enable tumor cells to obtain stemness property (Mani et al., 2008), therefore, we try to investigate whether EpCAM controls EMT progression. Immunofluorescence analyses illustrated the changes occurred in EMT markers (epithelial markers E-cadherin and cytokeratin 18 in up-regulations) and mesenchymal marker (vimentin in down-regulation) after knockdown of EpCAM (FIG. 11A). Real-time PCR data showed that an increase in E-cadherin with a concomitant decrease in vimentin in both mRNA and protein levels were detected in EpCAM knockdown cells, compared to that in vector alone cells (FIG. 11B). Other EMT-regulatory transcriptional factors, such as snail and slug, were simultaneously reduced in both EpCAM knockdown cells and EpCAM-low expressed cells (FIGS. 11B and 11C). Assessment of the effect of EpCAM on tumorigenic potential revealed that suppression of EpCAM resulted in the reduction of invasive and colony formation abilities in vitro (FIGS. 11D and 11E). Furthermore, suppression of EpCAM also inhibited xenograft tumor growth in vivo (FIG. 11F). RNA samples from primary tumor extraction demonstrated that expressions of EpCAM, reprogramming genes (c-Myc, Oct4, Nanog, and Sox2) and mesenchymal markers (vimentin and snail) were significantly diminished in EpCAM knockdown tumor cells, compared to that in vector alone (FIG. 11G). These data indicated that EpCAM is involved in regulating EMT progression and tumorigenesis.

Proteolytic Cleavage of EpICD Participates in EpCAM's Signaling Regulation

Figure 12:
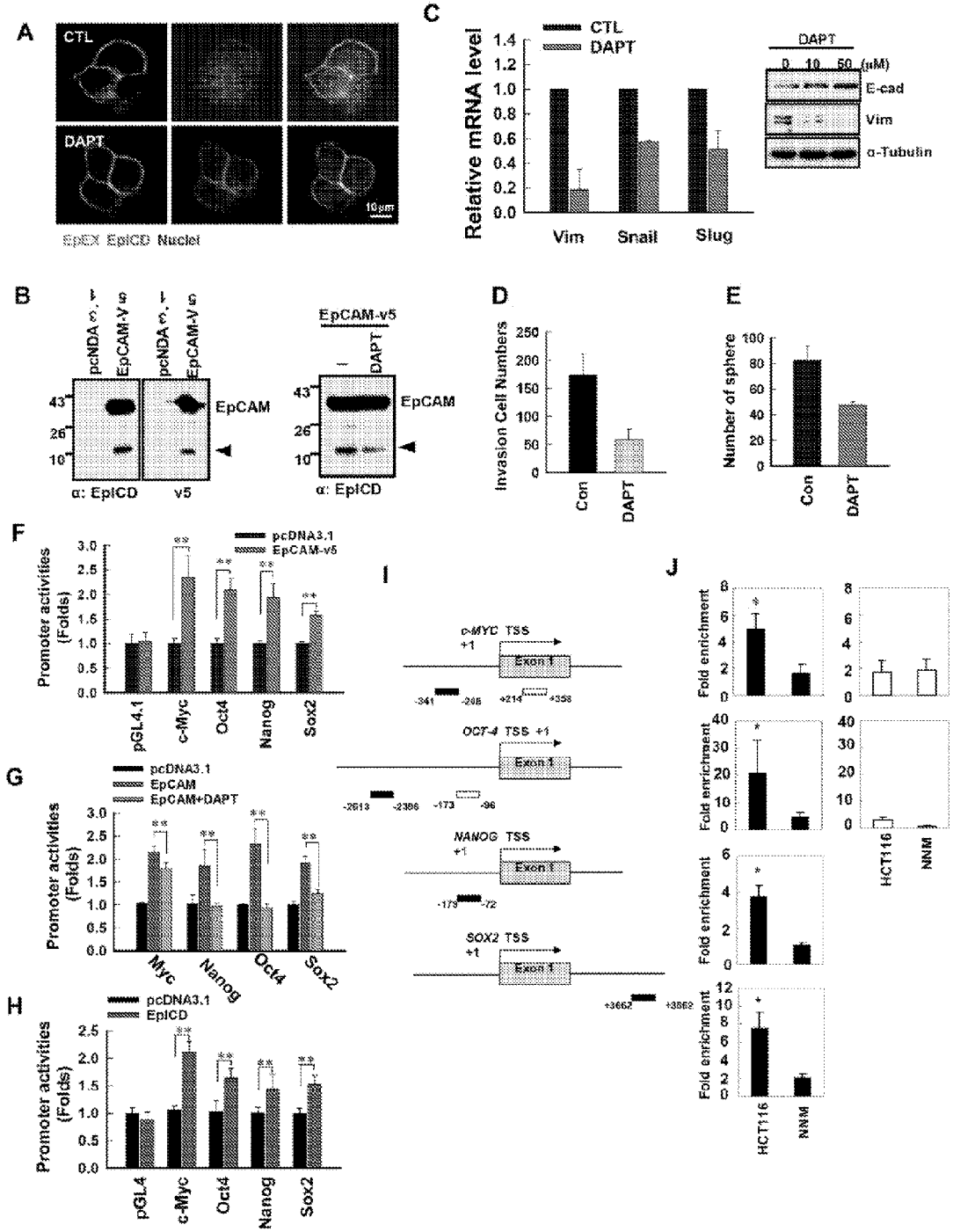
FIG. 12 shows EpICD Participates in Regulating Self-renewal and EMT genes. (A) Laser confocal immunofluorescence images of cellular localization of EpICD in HCT116 cells in the presence or absence of DAPT (50 µM). Bar=10 µm. (B) Western blot analysis of EpICD cleavage after treatment with DAPT in 293T/EpCAM-v5 cells, and protein samples were blotted with either EpICD or v5 antibody. (Black arrow indicated EpICD cleavage). (C-E) DAPT inhibits EMT genes expression (C), tumor invasion (D), and tumorsphere formation (E). (F) Overexpression of EpCAM up-regulates transcriptional activities of c-Myc. Oct4, Nanog, and Sox2. Promoter activities were assessed by luciferase assay. (G) DAPT inhibits EpCAM-induced c-Myc, Oct4, Nanog, and Sox2 transcriptional activities. (H) EpICD induction of transcriptional activation of reprogramming genes. (I-J) Chromatin immunoprecipitation (ChIP) analyzing DNA occupancy by EpICD on c-MYC, OCT4, NANOG, and SOX2 genes in HCT116 and NNM cells. ** p<0.01 denotes a significant difference.

The structure of EpCAM contains an extracellular domain (EpEX), a transmembrane domain, and an intracellular domain (EpICD). EpEx is composed of two epidermal growth factor-like domains and a cysteine-poor region, while EpICD is composed of a short 26-amino acid. The effect of EpICD on reprogramming gene regulation and tumorigenecity was examined. Laser confocal images depicted the soluble EpICD signals were detected in both cytoplasm and nucleus of HCT116 cells (FIG. 12A), whereas these scenarios were blocked in the presence of DAPT (a γ-secretase inhibitor). Most of EpICD showed co-localization with membrane-bound EpEX instead (FIG. 12A). In addition, soluble EpICD was expressed increasingly in spheroid-derived tumor section than that in adherent tumor section. Western blot analysis confirmed a dominant band with molecular weight in 40 kDa (EpCAM-v5), and a minor band lower than 10 kDa (EpICD-v5) in 293T/EpCAM-v5 cells; however, the expression of soluble EpICD-v5 (10 kDa) was reduced in the treatment of DAPT (FIG. 12B). Treatment with DAPT suppressed the expressions of vimentin, snail, and slug (FIG. 12C), which was accompanied by decreasing tumor invasiveness and sphere-forming capacity (FIGS. 12D and 12E). Further analysis of transcriptional regulation mediated by EpICD on reprogramming genes, co-transfections of EpCAM or EpICD with the tentative regulatory region of c-MYC, OCT4, NANOG, and SOX2 showed that both EpCAM and EpICD up-regulated transcriptional activities of the four genes (FIGS. 2F and 12H); however, these activations induced by EpCAM were blocked in the presence of DAPT (FIG. 12G). Moreover, chromatin immunoprecipitation assay indicating an occupancy of EpICD on c-MYC (proximal upstream region instead of exon 1), OCT4 (distal upstream region), NANOG (upstream region), and SOX2 (downstream region) promoters were detected in HCT116 cells (FIGS. 12I-J), whereas these phenomena were not found in normal nasal mucosa cells (NNM), which express rare level of EpCAM (data not shown).

Extracellular Domain of EpCAM Serves as an Activator for EpCAM's Signaling

Figure 13:
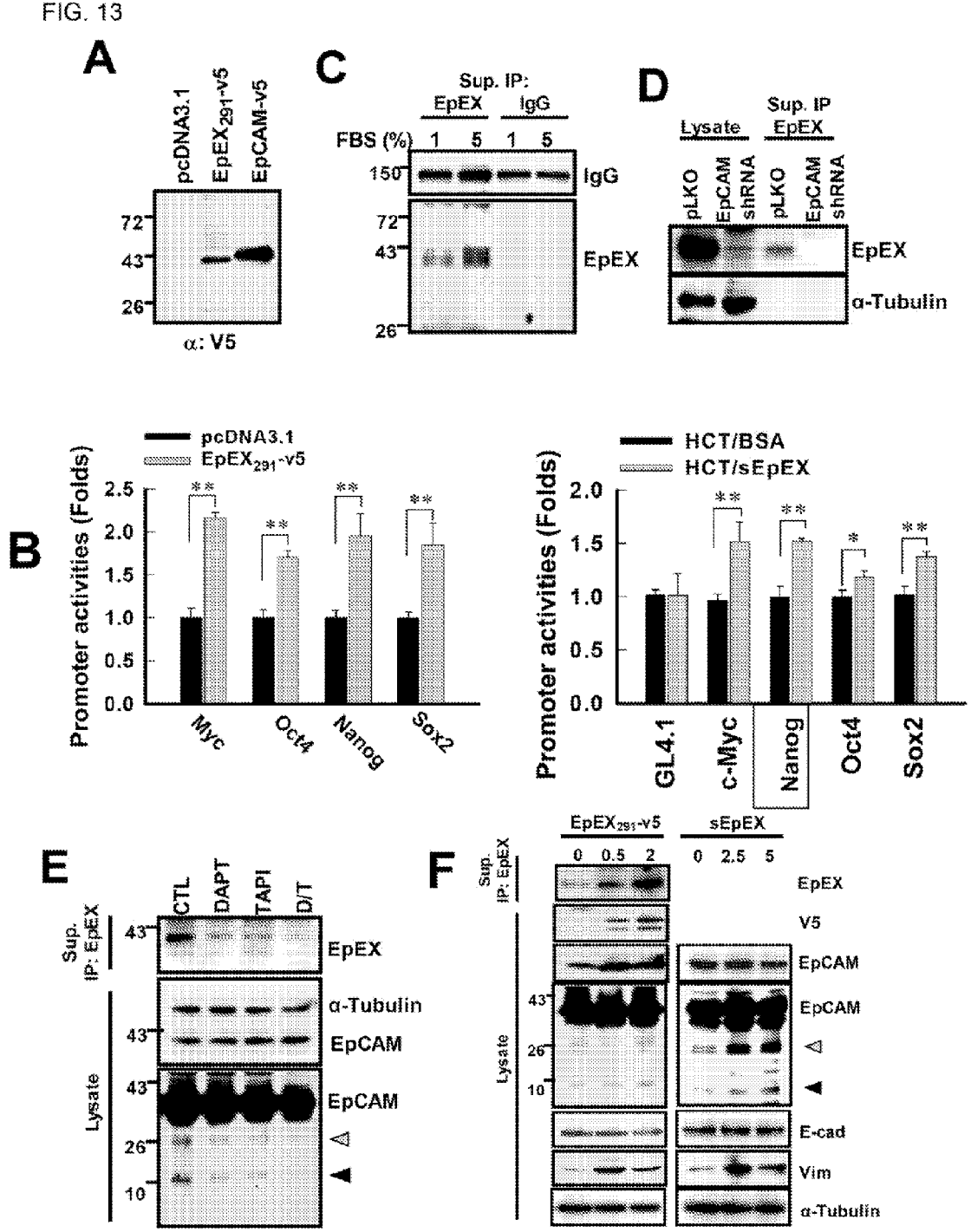
FIG. 13 shows EpEX serves as a Transducer for Activation of EpCAM-signaling. (A) Western blotting analysis of $EpEX_{291}$ and full-length EpCAM protein expression in 293T transfectants. (B) EpEX induces promoter activities of c-Myc, Nanog, Oct4, and Sox2. Cells were either transfected with pEpEX291 (left) or added soluble EpEX (sEpEX; 2 µg/ml) (right), reporter activities of c-Myc, Nanog, Oct4, and Sox2 were assessed by luciferase assay. BSA was used for control treatment. (C) Extracellular release of EpEX in EpCAM-expressed cells. Immunoprecipitation and Western blotting analyses of the releasing of EpEX level in culture supernatants (sup.) of HCT116 cells. (D) Identification of EpEX in culture supernatant from HCT/LKO and from HCT/EpCAM shRNA cells. (E) HCT116 cells were treated with DAPT (50 µM), TAPI (40 µM) or both (D/T) for 24 h, the culture supernatants were immunoprecipitated with EpEX antibody, and whole cell lysates (WCL) were subjected to Western blotting with anti-EpEX (middle panel) or anti-EpICD (lower panel) antibodies. Black arrow: soluble EpICD; gray arrow: intermediate EpICD. (F) HCT116 cells were transfected with pEpEX291-v5 (0.5, 2 µg) for 72 h (left) or treated with sEpEX (2.5, 5 µg/ml) (right), the culture supernatants and cell lysates were analyzed by Western blot as described above.
Figure 14:
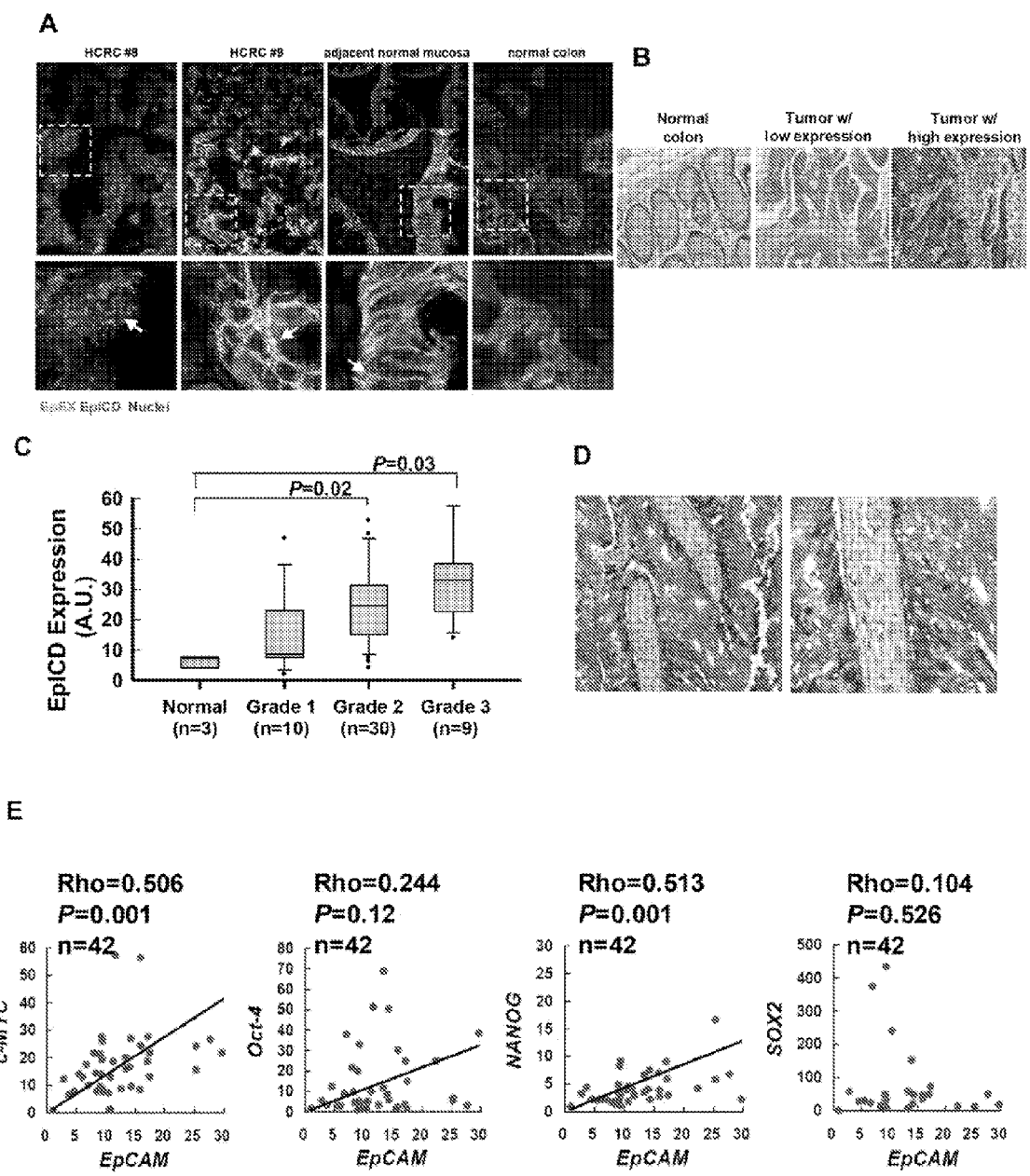
FIG. 14 shows correlation Between EpCAM (EpICD) with Self-renewal Gene Expression and Cancer Malignancy. (A) Immunofluorescent images of cellular localization of EpEX and EpICD in human colorectal carcinoma (HCRC), adjacent normal mucosa, and in normal colon tissue. Representative images are shown in separated image by EpEX (green) and EpICD (red) (upper panel), merged image (middle panel), and enlarged region from respective image (dash-box) (lower panel). Arrows indicate cellular localization of EpICD in the nucleus (HCRC) and in the membrane where colocalization with EpEX (adjacent normal mucosa) occurred. Immunohistochemistry analysis of EpICD protein expression by human colon cancer tissue microarray. Representative images are shown in randomly enlarged local view (B), and box plot of EpICD expression in normal and tumor with different grade was performed (C), P value was analyzed by t-test.

We further constructed an EpICD truncated vector (EpEX$_{291}$-v5), which contained the extracellular and transmembrane domains of EpCAM, (FIG. 13A) to discern the importance of EpICD in controlling reprogramming gene expression. Surprisingly, transfecting HCT116 cells with EpEX$_{291}$-v5 also induced reporter activities of c-MYC, OCT4, NANOG, and SOX2. Similar results were observed when treated with soluble EpEX (sEpEX) (FIG. 13B), suggesting that shedding or releasing of extracellular domain of EpCAM might also play a part in coordinating EpCAM's signaling. To test this hypothesis, cultured supernatant from HCT116 cells were immunoprecipitated with antibody against extracellular domain of EpCAM. Results showed that an increasing release of EpEX was identified in the presence of serum (FIG. 13C). The decreasing release of EpEX was further confirmed in the EpCAM knockdown cells (FIG. 13D). Moreover, treatments with DAPT (a γ-secretase inhibitor), TAPI (a TNF-α convening enzyme inhibitor), or both, blocked the release of EpEX and inhibited EpICD cleavage simultaneously. The membrane-bound EpCAM however was not affected by these treatments (FIG. 13E). Forced expression of EpEX$_{291}$-v5 in HCT 16 cells resulted in an increase of EpEX liberation in culture supernatants, and the inductions of EpICD cleavage and vimentin expression were detected both in EpEX$_{291}$-v5 transfectants and in sEpEX-treated cells (FIG. 13F). Moreover, Immunofluorescent analysis of human colon cancer specimens further revealed that parts of tumor cells expressing soluble EpICD in the nucleus lost their membrane-EpEX detection signal; whereas other tumor or its adjacent mucosa cells showed intact co-localization of EpICD and EpEX in the cell membrane. There was less expression of either EpEX or EpICD in normal colon tissue (FIG. 14A).

EpCAM/EpICD Expression in Human Colon Cancer Correlates with Reprogramming Factors We further analyzed the expression of EpCAM and EpICD with their association with reprogramming factors and tumor malignancy. Results showed that the expression of EpICD was increased in cancerous colon tissues when compared to that in the normal ones. The expression level of EpICD in cancer appeared to be associated with tumor grade, although this difference did not achieve statistical significance (FIGS. 14B-C). We also found that in some tumor tissues (24 of 49 cases) with nuclear EpICD expression, the positive area presented was much less within the whole region. Most signals were detected in the cytosolic or membrane compartment (FIG. 14D), suggesting that nuclear translocation of EpICD may be a dynamically transient regulation. Further evaluation of the mRNA level in EpCAM and its correlation with the four reprogramming factors from forty-two colon cancer panel indicated that the expression of EpCAM was positively correlated with c-MYC (coefficiency=0.501; moderate correlation), NANOG (coefficiency=0.513; moderate correlation), and OCT4 (coefficiency=0.244; minor correlation) (FIG. 14E).

In conclusion, it was demonstrated that co-expressions of EpCAM and stenmness genes are elevated in TICs. EpCAM upregulates both reprogramming factors (c-Myc, Oct4, Nanog, and Sox2) and EMT expressions. Proteolysis of EpCAM into EpEX and EpICD played an important role in mediating EpCAM's signaling. Nuclear translocation of EpICD regulates reprogramming gene expression while extracellular releasing of EpEX triggers further activation of EpICD. Suppression of EpCAM or blocking of EpICD cleavage decreases invasiveness, growth, and self-renewal ability both in vitro and in vivo. The results indicate that overexpression of EpCAM helps promote tumor-initiation and tumor-progression. The EpCAM mAbs can be used for cancer diagnosis and prognosis, and cancer-targeted therapy and imaging.

EpCAM, or epithelial specific antigen (ESA), is a carcinoma-specific antigen in identifying epithelial-transformed neoplasia. Overexpression of EpCAM is associated with metastatic, drug resistant, and circulating tumor cells, which are all characteristics of TICs. Several studies have successfully identified TICs within pancreatic, ovarian, hepatic, and colorectal cancers through immunoassay staining using $CD44^+/CD24^-$ in conjunction with EpCAM. The data here demonstrated that upregulation of EpCAM was identified in culture of tumorsphere, which exhibited great potential in tumor initiation, growth, and invasiveness; however, the self-renewal and initiating abilities were inhibited after knocking down of EpCAM. Alternatively, loss-of function of EpCAM in tumor cells suppressed clonal growth, invasiveness, and tumorigenesis. We also found that increased expression of EpCAM is associated with tumor grade, demonstrating the critical role of EpCAM in tumor progression.

Although the relevance of EpCAM and TICs in the formation of tumor has been well documented, genetic profile regulated by EpCAM in TICs is still unclear. There still lacks direct evidence linking the reciprocation of these genes to TICs. Our data showed that elevated and persisted expressions of EpCAM were detected concomitantly with the presence of c-Myc, Oct4, Nanog, and Sox2 in tumorsphere and sphere-derived xenografts. Gain- or -loss of function in EpCAM directly impacted the production of these genes, and luciferase assay identified that these genes were regulated by EpCAM. Cancer tissue mRNA array data further confirmed the expression of EpCAM to be positively correlated with c-Myc, Oct4, Nanog, and Sox2. Collectively, these data indicated that directly regulation of reprogramming factors by EpCAM may promote tumor initiation.

In addition to stenmness genes, the promotion of epithelial-mesenchymal transition may also "participate" in EpCAM-mediated tumor progression. Our data found that both upregulations of snail, slug, and vimentin, and down-regulation of E-cadherin, were detected in EpCAM overexpression cells. Conversely, knockdown of EpCAM or addition of DAPT, which blocked the releasing of EpICD, suppressed the mRNA levels of snail, slug, and vimentin, which was accompanied with the reduction of tumor invasion.

EpICD is regulated by proteolysis by TNF-α converting enzyme (TACE) and γ-secretase (presenilin 2; PS2), followed by collaboration with FHL2 and Tcf/Lef1. We found that accumulations of soluble EpICD in both cytoplasm and nucleus were detected consistently in cultured tumor cells, sphere-derived tumor xenograft, and human colon cancers. Chromatin immunoprecipitation and luciferase assays indicated that EpICD bound to and transactivated reprogramming gene. Treatment with γ-secretase inhibitors blocked cleavage and nuclear translocation of EpICD, which was accompanied by the suppression of reprogramming factors and EMT gene expressions, thereby inhibiting tumor self-renewal and invasiveness. However, the presence of soluble EpICD in either cytoplasm or nucleus was not expressed homogenously in all tumor cells, suggesting that the cleavage of EpICD might be a dynamical process. In addition to EpICD, we also found that releasing of EpEX may trigger EpCAM's signaling event. The release of EpEX in supernatants was increased by serum concentration, and the addition of either DAPT or TAPI blocked the liberation of EpEX and EpICD. Moreover, treatment of sEpEX or transfection with pEpEX promoted cleavage of EpICD and induced reprogramming gene activations, suggesting that the cleavage of EpEX may initialize EpCAM's signaling and that its release may further trigger EpCAM's activation.

The invention relates to novel EpCAM mAbs with extreme binding affinity against EpCAM, which displayed effective tumor inhibitory activity and thus could provide promising therapeutic meaning. Collectively, we show the comprehensive evidence demonstrate that elevation of EpCAM, especially EpICD, promotes tumorigenesis in TICs through upregulation of stemness genes expressions and EMT process. Furthermore, releasing of EpEX may trigger EpCAM's signaling event via autocrine or paracrine effect. Therefore, development and application of inhibitors or antibodies for EpCAM and/or EpEX in either treating or detecting are helpful to eradicate tumor and TICs as well as for tumor targeting imaging.

What is claimed is:

1. An isolated monoclonal antibody or an antigen-binding fragment thereof that has a specific binding affinity to an epitope within the sequence of KPEGALQNNDGLYDPDCDE (SEQ ID NO: 63) located within the EGF-like domain II of epithelial cell adhesion molecule (EpCAM, SEQ ID NO: 1).

2. The antibody or antigen-binding fragment of claim 1, which is characterized by:
said binding affinity is abrogated when Tyrosine at amino acid position 95 ($Y_{95}$), Aspartic acid at amino acid position 96 ($D_{96}$), or both Tyrosine ($Y_{95}$) and Aspartic acid ($D_{96}$) within the EGF-like domain II of EpCam are mutated.

3. The antibody or binding fragment of claim 1, comprising:
(a) a heavy chain variable region, comprising:
(i) complementarity determining region 1 (CDR1) comprising SEQ ID NO: 4;
(ii) complementarity determining region 2 (CDR2) comprising SEQ ID NO: 5; and
(iii) complementarity determining region 3 (CDR3) comprising SEQ ID NO: 6; and
(b) a light chain variable region, comprising:
(i) CDR1 comprising SEQ ID NO: 7;
(ii) CDR2 comprising SEQ ID NO: 8; and
(iii) CDR3 comprising SEQ ID NO: 9.

4. The antibody or binding fragment of claim 1, wherein the binding fragment comprises an Fv fragment of the antibody.

5. The antibody or binding fragment of claim 1, wherein the binding fragment comprises an Fab fragment of the antibody.

6. The antibody or antigen-binding fragment of claim 1, wherein the antibody or antigen-binding fragment is humanized.

7. The antibody or antigen-binding, fragment of claim 6. wherein the heavy chain variable region comprises the amino acid sequence of SEQ ID NO: 24, and the light chain variable region comprises the amino acid sequence of SEQ ID NO: 25.

8. An isolated single-chain variable fragment comprising:
(a) a heavy chain variable region comprising the amino acid sequence of SEQ ID NO: 2 and a light chain variable region comprising the amino acid sequence of SEQ ID NO: 3, or a heavy chain variable region comprising the amino acid sequence of SEQ ID NO: 24 and a light chain variable region comprising the amino acid sequence of SEQ ID NO: 25; and
(b) a linker peptide connecting the heavy chain variable region and the light chain variable region.

9. An isolated monoclonal antibody or antigen-binding fragment thereof, said antibody being characterized by:
(a) having a specific binding affinity to epithelial cell adhesion molecule (EpCAM)comprising the amino acid sequence of SEQ ID NO: 1;
(b) having a specific binding affinity to cancer cells expressing EpCAM, said cancer cells being selected from the group consisting of oral cancer cells, nasopharyngeal cancer cells, colorectal cancer cells, and ovarian cancer cells; and
(c) having no binding affinity to human umbilical vein endothelial cell and normal nasal mucosal epithelia:
wherein said antibody or antigen-binding fragment exhibits a specific binding affinity to an epitope within the sequence of KPEGALQNNDGLADPDCDE (SEQ ID NO: 63) located within the EGF-like domain II of EpCam (SEQ ID No: 1).

10. The antibody or antigen-binding fragment of claim 9, wherein said antibody or antigen-binding fragment exhibits a characteristic of inducing apoptosis of said cancer cells and/or inhibiting growth of said cancer cells in vivo.

11. The antibody or antigen-binding fragment of claim 9, comprising:
(a) a heavy chain variable region comprising the amino acid sequence of SEQ ID NO: 2 and a light chain variable region comprising the amino acid sequence of SEQ ID NO: 3; or
(b) a heavy chain variable region comprising the amino acid sequence of SEQ ID NO: 24 and a light chain variable region comprising the amino acid sequence of SEQ ID NO: 25.

12. The antibody or antigen-binding fragment of claim 9, wherein the antibody or antigen-binding fragment is humanized.

13. A method of inhibiting growth of cancer cells and/or tumor-initiating cells, comprising:
administering to a subject in need thereof a composition that comprises:
(a) the antibody or antigen-binding fragment of claim 10; and
(b) a pharmaceutically acceptable carrier,
wherein said cancer cells and/or tumor-initiating cells express EpCAM.

14. A method of detecting and/or diagnosing cancer cells that expresses EpCAM in vitro, the method comprising:
(a) obtaining a cell or a tissue sample from a patient;
(b) contacting the cell or the tissue sample with the antibody or binding fragment of claim 9;
(c) assaying the binding of the antibody or binding fragment to the cell or tissue sample; and
(d) comparing the binding with a normal control to determine the presence of the cancer cells that expresses EpCAM in the subject.

15. The method of claim 13, wherein the antibody or antigen-binding fragment comprises:
(a) a heavy chain variable region comprising the amino acid sequence of SEQ ID NO: 24 and a light chain variable region comprising the amino acid sequence of SEQ ID NO: 25; or
(b) a heavy chain variable region comprising the amino acid sequence of SEQ ID NO: 2 and a light chain variable region comprising the amino acid sequence of SEQ ID NO: 3.

16. The method of claim 13, wherein the antibody or antigen-binding fragment is humanized.

17. The method of claim 13, wherein the cancer cells are selected from the group consisting of oral cancer cells, nasopharyngeal cancer cells, colorectal cancer cells, and ovarian cancer cells.

18. The antibody or antigen-binding fragment a claim 1, which is labeled by a detectable compound or an enzyme, or is encapsulated within a liposome.

19. A composition comprising:
(a) an isolated antibody or antigen-binding fragment of claim 6;
(b) an anti-cancer agent; and
(c) a pharmaceutically acceptable carrier.

20. A method of inhibiting growth of cancer cells and/or tumor-initiating cells, comprising:
administering to a subject in need thereof a composition that comprises:
(a) the antibody or antigen-binding fragment of claim 1; and
(b) a pharmaceutically acceptable carrier,
wherein said cancer cells and/or tumor-initiating cells express EpCAM.

* * * * *

SEQUENCE LISTING

```
<160> NUMBER OF SEQ ID NOS: 73

<210> SEQ ID NO 1
<211> LENGTH: 314
<212> TYPE: PRT
<213> ORGANISM: Homo sapiens

<400> SEQUENCE: 1
```

```
Met Ala Pro Pro Gln Val Leu Ala Phe Gly Leu Leu Leu Ala Ala
1               5                   10                  15

Thr Ala Thr Phe Ala Ala Ala Gln Glu Cys Val Cys Glu Asn Tyr
            20                  25                  30

Lys Leu Ala Val Asn Cys Phe Val Asn Asn Arg Gln Cys Gln Cys
            35                  40                  45

Thr Ser Val Gly Ala Gln Asn Thr Val Ile Cys Ser Lys Leu Ala Ala
            50                  55                  60

Lys Cys Leu Val Met Lys Ala Glu Met Asn Gly Ser Lys Leu Gly Arg
65                  70                  75                  80

Arg Ala Lys Pro Glu Gly Ala Leu Gln Asn Asn Asp Gly Leu Tyr Asp
                85                  90                  95

Pro Asp Cys Asp Glu Ser Gly Leu Phe Lys Ala Lys Gln Cys Asn Gly
                100                 105                 110

Thr Ser Met Cys Trp Cys Val Asn Thr Ala Gly Val Arg Arg Thr Asp
            115                 120                 125

Lys Asp Thr Glu Ile Thr Cys Ser Glu Arg Val Arg Thr Tyr Trp Ile
            130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
                165                 170                 175

Asp Pro Lys Phe Ile Thr Ser Ile Leu Tyr Glu Asn Asn Val Ile Thr
                180                 185                 190

Ile Asp Leu Val Gln Asn Ser Ser Gln Lys Thr Gln Asn Asp Val Asp
                195                 200                 205

Ile Ala Asp Val Ala Tyr Tyr Phe Glu Lys Asp Val Lys Gly Glu Ser
                210                 215                 220

Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
                245                 250                 255

Pro Glu Phe Ser Met Gln Gly Leu Lys Ala Gly Val Ile Ala Val Ile
                260                 265                 270

Val Val Val Val Ile Ala Val Val Ala Gly Ile Val Val Leu Val Ile
                275                 280                 285

Ser Arg Lys Lys Arg Met Ala Lys Tyr Glu Lys Ala Glu Ile Lys Glu
                290                 295                 300

Met Gly Glu Met His Arg Glu Leu Asn Ala
305                 310

<210> SEQ ID NO 2
<211> LENGTH: 113
<212> TYPE: PRT
<213> ORGANISM: Homo sapiens

<400> SEQUENCE: 2

Glu Val Gln Leu Val Glu Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
            35                  40                  45

Gly Trp Ile Asn Thr Glu Thr Gly Glu Pro Thr Phe Ala Asp Asp Phe
```

```
                50                  55                  60
Lys Gly Arg Phe Ala Phe Ser Leu Glu Thr Ser Ala Arg Thr Thr Tyr
 65                  70                  75                  80

Leu Gln Ile Asn Asn Leu Lys Asn Glu Asp Thr Ala Thr Tyr Phe Cys
                 85                  90                  95

Ala Arg Thr Ala Val Tyr Trp Gly Gln Gly Thr Ser Leu Thr Val Ser
            100                 105                 110

Ser

<210> SEQ ID NO 3
<211> LENGTH: 116
<212> TYPE: PRT
<213> ORGANISM: Homo sapiens

<400> SEQUENCE: 3

Asp Ile Gln Leu Thr Gln Ser Pro Ser Ser Leu Ser Ala Ser Leu Gly
  1               5                  10                  15

Glu Arg Val Ser Leu Thr Cys Arg Ala Ser Gln Glu Ile Ser Val Ser
             20                  25                  30

Leu Ser Trp Leu Gln Gln Lys Pro Asp Gly Thr Ile Lys Arg Leu Ile
         35                  40                  45

Tyr Ala Thr Ser Thr Leu Asp Ser Gly Val Pro Lys Arg Phe Ser Gly
     50                  55                  60

Ser Arg Ser Gly Ser Asp Tyr Ser Leu Thr Ile Ser Ser Leu Glu Ser
 65                  70                  75                  80

Glu Asp Phe Ala Asp Tyr Tyr Cys Leu Gln Tyr Ala Ser Tyr Pro Trp
                 85                  90                  95

Thr Phe Gly Gly Gly Thr Lys Leu Glu Ile Lys Arg Ala Asp Ala Ala
            100                 105                 110

Pro Thr Val Ser
        115

<210> SEQ ID NO 4
<211> LENGTH: 10
<212> TYPE: PRT
<213> ORGANISM: Homo sapiens

<400> SEQUENCE: 4

Gly Tyr Thr Phe Thr Asp Tyr Ser Met His
  1               5                  10

<210> SEQ ID NO 5
<211> LENGTH: 8
<212> TYPE: PRT
<213> ORGANISM: Homo sapiens

<400> SEQUENCE: 5

Ile Asn Thr Glu Thr Gly Glu Pro
  1               5

<210> SEQ ID NO 6
<211> LENGTH: 4
<212> TYPE: PRT
<213> ORGANISM: Homo sapiens

<400> SEQUENCE: 6

Thr Ala Val Tyr
  1
```

```
<210> SEQ ID NO 7
<211> LENGTH: 11
<212> TYPE: PRT
<213> ORGANISM: Homo sapiens

<400> SEQUENCE: 7

Arg Ala Ser Gln Glu Ile Ser Val Ser Leu Ser
1               5                   10

<210> SEQ ID NO 8
<211> LENGTH: 7
<212> TYPE: PRT
<213> ORGANISM: Homo sapiens

<400> SEQUENCE: 8

Ala Thr Ser Thr Leu Asp Ser
1               5

<210> SEQ ID NO 9
<211> LENGTH: 9
<212> TYPE: PRT
<213> ORGANISM: Homo sapiens

<400> SEQUENCE: 9

Leu Gln Tyr Ala Ser Tyr Pro Trp Thr
1               5

<210> SEQ ID NO 10
<211> LENGTH: 25
<212> TYPE: PRT
<213> ORGANISM: Homo sapiens

<400> SEQUENCE: 10

Glu Val Gln Leu Val Glu Ser Gly Pro Glu Leu Lys Lys Pro Gly Glu
1               5                   10                  15

Thr Val Lys Ile Ser Cys Lys Ala Ser
            20                  25

<210> SEQ ID NO 11
<211> LENGTH: 15
<212> TYPE: PRT
<213> ORGANISM: Homo sapiens

<400> SEQUENCE: 11

Trp Val Lys Gln Ala Pro Gly Lys Gly Leu Lys Trp Met Gly Trp
1               5                   10                  15

<210> SEQ ID NO 12
<211> LENGTH: 40
<212> TYPE: PRT
<213> ORGANISM: Homo sapiens

<400> SEQUENCE: 12

Thr Phe Ala Asp Asp Phe Lys Gly Arg Phe Ala Phe Ser Leu Glu Thr
1               5                   10                  15

Ser Ala Arg Thr Thr Tyr Leu Gln Ile Asn Asn Leu Lys Asn Glu Asp
            20                  25                  30

Thr Ala Thr Tyr Phe Cys Ala Arg
            35                  40

<210> SEQ ID NO 13
<211> LENGTH: 11
<212> TYPE: PRT
<213> ORGANISM: Homo sapiens
```

```
<400> SEQUENCE: 13

Trp Gly Gln Gly Thr Ser Leu Thr Val Ser Ser
1               5                   10

<210> SEQ ID NO 14
<211> LENGTH: 23
<212> TYPE: PRT
<213> ORGANISM: Homo sapiens

<400> SEQUENCE: 14

Asp Ile Gln Leu Thr Gln Ser Pro Ser Leu Ser Ala Ser Leu Gly
1               5                   10                  15

Glu Arg Val Ser Leu Thr Cys
            20

<210> SEQ ID NO 15
<211> LENGTH: 15
<212> TYPE: PRT
<213> ORGANISM: Homo sapiens

<400> SEQUENCE: 15

Trp Leu Gln Gln Lys Pro Asp Gly Thr Ile Lys Arg Leu Ile Tyr
1               5                   10                  15

<210> SEQ ID NO 16
<211> LENGTH: 32
<212> TYPE: PRT
<213> ORGANISM: Homo sapiens

<400> SEQUENCE: 16

Gly Val Pro Lys Arg Phe Ser Gly Ser Arg Ser Gly Ser Asp Tyr Ser
1               5                   10                  15

Leu Thr Ile Ser Ser Leu Glu Ser Glu Asp Phe Ala Asp Tyr Tyr Cys
            20                  25                  30

<210> SEQ ID NO 17
<211> LENGTH: 19
<212> TYPE: PRT
<213> ORGANISM: Homo sapiens

<400> SEQUENCE: 17

Phe Gly Gly Gly Thr Lys Leu Glu Ile Lys Arg Ala Asp Ala Ala Pro
1               5                   10                  15

Thr Val Ser

<210> SEQ ID NO 18
<211> LENGTH: 24
<212> TYPE: PRT
<213> ORGANISM: Artificial Sequence
<220> FEATURE:
<223> OTHER INFORMATION: humanized VH domain FW1

<400> SEQUENCE: 18

Val Lys Leu Gln Glu Ser Gly Pro Glu Leu Lys Lys Pro Gly Glu Thr
1               5                   10                  15

Val Lys Ile Ser Cys Lys Ala Ser
            20

<210> SEQ ID NO 19
<211> LENGTH: 40
<212> TYPE: PRT
<213> ORGANISM: Artificial Sequence
```

-continued

<220> FEATURE:
<223> OTHER INFORMATION: Humanized VH domain FW3

<400> SEQUENCE: 19

Thr Tyr Ala Asp Asp Phe Lys Gly Arg Phe Ala Phe Ser Leu Glu Thr
1               5                   10                  15

Ser Ala Ser Thr Ala Tyr Leu Gln Ile Asn Asn Leu Lys Asn Glu Asp
            20                  25                  30

Thr Ala Thr Tyr Phe Cys Ala Arg
        35                  40

<210> SEQ ID NO 20
<211> LENGTH: 11
<212> TYPE: PRT
<213> ORGANISM: Artificial Sequence
<220> FEATURE:
<223> OTHER INFORMATION: Humanized VH domain FW4

<400> SEQUENCE: 20

Trp Gly Gln Gly Thr Thr Val Thr Val Ser Ser
1               5                   10

<210> SEQ ID NO 21
<211> LENGTH: 23
<212> TYPE: PRT
<213> ORGANISM: Artificial Sequence
<220> FEATURE:
<223> OTHER INFORMATION: Humanized VL domain FW1

<400> SEQUENCE: 21

Asp Ile Gln Met Thr Gln Ser Pro Ser Ser Leu Ser Ala Ser Leu Gly
1               5                   10                  15

Glu Arg Val Ser Leu Thr Cys
            20

<210> SEQ ID NO 22
<211> LENGTH: 15
<212> TYPE: PRT
<213> ORGANISM: Artificial Sequence
<220> FEATURE:
<223> OTHER INFORMATION: Humanized VL domain FW2

<400> SEQUENCE: 22

Trp Leu Gln Gln Glu Pro Asp Gly Thr Ile Lys Arg Leu Ile Tyr
1               5                   10                  15

<210> SEQ ID NO 23
<211> LENGTH: 32
<212> TYPE: PRT
<213> ORGANISM: Artificial Sequence
<220> FEATURE:
<223> OTHER INFORMATION: Humanized VL domain FW3

<400> SEQUENCE: 23

Gly Val Pro Lys Arg Phe Ser Gly Ser Arg Ser Gly Ser Asp Tyr Ser
1               5                   10                  15

Leu Thr Ile Ser Ser Leu Glu Ser Glu Asp Phe Val Asp Tyr Tyr Cys
            20                  25                  30

<210> SEQ ID NO 24
<211> LENGTH: 112
<212> TYPE: PRT
<213> ORGANISM: Artificial Sequence
<220> FEATURE:
<223> OTHER INFORMATION: Humanized VH domain

<400> SEQUENCE: 24

Val Lys Leu Gln Glu Ser Gly Pro Glu Leu Lys Pro Gly Glu Thr
1               5                   10                  15

Val Lys Ile Ser Cys Lys Ala Ser Gly Tyr Thr Phe Thr Asp Tyr Ser
                20                  25                  30

Met His Trp Val Lys Gln Ala Pro Gly Lys Gly Leu Lys Trp Met Gly
            35                  40                  45

Trp Ile Asn Thr Glu Thr Gly Glu Pro Thr Tyr Ala Asp Asp Phe Lys
50                  55                  60

Gly Arg Phe Ala Phe Ser Leu Glu Thr Ser Ala Ser Thr Ala Tyr Leu
65                  70                  75                  80

Gln Ile Asn Asn Leu Lys Asn Glu Asp Thr Ala Thr Tyr Phe Cys Ala
                85                  90                  95

Arg Thr Ala Val Tyr Trp Gly Gln Gly Thr Thr Val Thr Val Ser Ser
            100                 105                 110

<210> SEQ ID NO 25
<211> LENGTH: 116
<212> TYPE: PRT
<213> ORGANISM: Artificial Sequence
<220> FEATURE:
<223> OTHER INFORMATION: Humanized VL domain

<400> SEQUENCE: 25

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Val Ser
                20                  25                  30

Leu Ser Trp Leu Gln Gln Glu Pro Asp Gly Thr Ile Lys Arg Leu Ile
            35                  40                  45

Tyr Ala Thr Ser Thr Leu Asp Ser Gly Val Pro Lys Arg Phe Ser Gly
50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Tyr Pro Trp
                85                  90                  95

Thr Phe Gly Gly Gly Thr Lys Leu Glu Ile Lys Arg Ala Asp Ala Ala
            100                 105                 110

Pro Thr Val Ser
        115

<210> SEQ ID NO 26
<211> LENGTH: 18
<212> TYPE: DNA
<213> ORGANISM: Artificial Sequence
<220> FEATURE:
<223> OTHER INFORMATION: EpCAM F Primer

<400> SEQUENCE: 26
ctccacgtgc tggtgtgt                                                 18

<210> SEQ ID NO 27
<211> LENGTH: 26
<212> TYPE: DNA
<213> ORGANISM: Artificial Sequence
<220> FEATURE:
<223> OTHER INFORMATION: EpCAM R Primer

<400> SEQUENCE: 27

```
tgttttagtt caatgatgat ccagta                                         26

<210> SEQ ID NO 28
<211> LENGTH: 22
<212> TYPE: DNA
<213> ORGANISM: Artificial Sequence
<220> FEATURE:
<223> OTHER INFORMATION: c-Myc F Primer

<400> SEQUENCE: 28
aaacacaaac ttgaacagct ac                                             22

<210> SEQ ID NO 29
<211> LENGTH: 23
<212> TYPE: DNA
<213> ORGANISM: Artificial Sequence
<220> FEATURE:
<223> OTHER INFORMATION: c-Myc R Primer

<400> SEQUENCE: 29
atttgaggca gtttacatta tgg                                            23

<210> SEQ ID NO 30
<211> LENGTH: 20
<212> TYPE: DNA
<213> ORGANISM: Artificial Sequence
<220> FEATURE:
<223> OTHER INFORMATION: nanog F Primer

<400> SEQUENCE: 30
atgcctcaca cggagactgt                                                20

<210> SEQ ID NO 31
<211> LENGTH: 20
<212> TYPE: DNA
<213> ORGANISM: Artificial Sequence
<220> FEATURE:
<223> OTHER INFORMATION: Nanog R Primer

<400> SEQUENCE: 31
agggctgtcc tgaataagca                                                20

<210> SEQ ID NO 32
<211> LENGTH: 21
<212> TYPE: DNA
<213> ORGANISM: Artificial Sequence
<220> FEATURE:
<223> OTHER INFORMATION: Sox2 F Primer

<400> SEQUENCE: 32
tatttgaatc agtctgccga g                                              21

<210> SEQ ID NO 33
<211> LENGTH: 28
<212> TYPE: DNA
<213> ORGANISM: Artificial Sequence
<220> FEATURE:
<223> OTHER INFORMATION: Sox2 R Primer

<400> SEQUENCE: 33
atgtacctgt tataaggatg atattagt                                       28

<210> SEQ ID NO 34
<211> LENGTH: 18
<212> TYPE: DNA
```

```
<213> ORGANISM: Artificial Sequence
<220> FEATURE:
<223> OTHER INFORMATION: Oct4 F Primer

<400> SEQUENCE: 34
agcaaaaccc ggaggagt                                                 18

<210> SEQ ID NO 35
<211> LENGTH: 21
<212> TYPE: DNA
<213> ORGANISM: Artificial Sequence
<220> FEATURE:
<223> OTHER INFORMATION: Oct4 R Primer

<400> SEQUENCE: 35
ccacatcggc ctgtgtatat c                                             21

<210> SEQ ID NO 36
<211> LENGTH: 22
<212> TYPE: DNA
<213> ORGANISM: Artificial Sequence
<220> FEATURE:
<223> OTHER INFORMATION: E-cadherin F Primer

<400> SEQUENCE: 36
ggaactatga aaagtgggct tg                                            22

<210> SEQ ID NO 37
<211> LENGTH: 20
<212> TYPE: DNA
<213> ORGANISM: Artificial Sequence
<220> FEATURE:
<223> OTHER INFORMATION: E-cadherin R Primer

<400> SEQUENCE: 37
aaattgccag gctcaatgac                                               20

<210> SEQ ID NO 38
<211> LENGTH: 20
<212> TYPE: DNA
<213> ORGANISM: Artificial Sequence
<220> FEATURE:
<223> OTHER INFORMATION: Vimentin F Primer

<400> SEQUENCE: 38
gtttccccta aaccgctagg                                               20

<210> SEQ ID NO 39
<211> LENGTH: 18
<212> TYPE: DNA
<213> ORGANISM: Artificial Sequence
<220> FEATURE:
<223> OTHER INFORMATION: Vimentin R Primer

<400> SEQUENCE: 39
agcgagagtg gcagagga                                                 18

<210> SEQ ID NO 40
<211> LENGTH: 19
<212> TYPE: DNA
<213> ORGANISM: Artificial Sequence
<220> FEATURE:
<223> OTHER INFORMATION: Snail F Primer

<400> SEQUENCE: 40
cttcggctcc aggagagtc                                                19
```

```
<210> SEQ ID NO 41
<211> LENGTH: 21
<212> TYPE: DNA
<213> ORGANISM: Artificial Sequence
<220> FEATURE:
<223> OTHER INFORMATION: Snail R Primer

<400> SEQUENCE: 41
ttcccactgt cctcatctga c                                              21

<210> SEQ ID NO 42
<211> LENGTH: 20
<212> TYPE: DNA
<213> ORGANISM: Artificial Sequence
<220> FEATURE:
<223> OTHER INFORMATION: Slug F Primer

<400> SEQUENCE: 42
tggttgcttc aaggacacat                                                20

<210> SEQ ID NO 43
<211> LENGTH: 19
<212> TYPE: DNA
<213> ORGANISM: Artificial Sequence
<220> FEATURE:
<223> OTHER INFORMATION: Slug R Primer

<400> SEQUENCE: 43
gttgcagtga gggcaagaa                                                 19

<210> SEQ ID NO 44
<211> LENGTH: 21
<212> TYPE: DNA
<213> ORGANISM: Artificial Sequence
<220> FEATURE:
<223> OTHER INFORMATION: GAPDH F Primer

<400> SEQUENCE: 44
cttcaccacc atggaggagg c                                              21

<210> SEQ ID NO 45
<211> LENGTH: 21
<212> TYPE: DNA
<213> ORGANISM: Artificial Sequence
<220> FEATURE:
<223> OTHER INFORMATION: GAPDH R Primer

<400> SEQUENCE: 45
ggcatggact gtggtcatga g                                              21

<210> SEQ ID NO 46
<211> LENGTH: 20
<212> TYPE: DNA
<213> ORGANISM: Artificial Sequence
<220> FEATURE:
<223> OTHER INFORMATION: 18s rRNA F Primer

<400> SEQUENCE: 46
gcaattattc cccatgaacg                                                20

<210> SEQ ID NO 47
<211> LENGTH: 20
<212> TYPE: DNA
<213> ORGANISM: Artificial Sequence
<220> FEATURE:
```

```
<223> OTHER INFORMATION: 18s rRNA R Primer

<400> SEQUENCE: 47
gggacttaat caacgcaagc                                              20

<210> SEQ ID NO 48
<211> LENGTH: 22
<212> TYPE: DNA
<213> ORGANISM: Artificial Sequence
<220> FEATURE:
<223> OTHER INFORMATION: ChIP primers c-Myc F

<400> SEQUENCE: 48
gcctgcgatg atttatactc ac                                           22

<210> SEQ ID NO 49
<211> LENGTH: 19
<212> TYPE: DNA
<213> ORGANISM: Artificial Sequence
<220> FEATURE:
<223> OTHER INFORMATION: ChIP primers c-Myc R

<400> SEQUENCE: 49
aaacagagta agagagccg                                               19

<210> SEQ ID NO 50
<211> LENGTH: 20
<212> TYPE: DNA
<213> ORGANISM: Artificial Sequence
<220> FEATURE:
<223> OTHER INFORMATION: ChIP primers Nanog F

<400> SEQUENCE: 50
tcttcaggtt ctgttgctcg                                              20

<210> SEQ ID NO 51
<211> LENGTH: 22
<212> TYPE: DNA
<213> ORGANISM: Artificial Sequence
<220> FEATURE:
<223> OTHER INFORMATION: ChIP primers Nanog R

<400> SEQUENCE: 51
gttaatcccg tctaccagtc tc                                           22

<210> SEQ ID NO 52
<211> LENGTH: 26
<212> TYPE: DNA
<213> ORGANISM: Artificial Sequence
<220> FEATURE:
<223> OTHER INFORMATION: ChIP Primers Sox2 F

<400> SEQUENCE: 52
ggataacatt gtactgggaa gggaca                                       26

<210> SEQ ID NO 53
<211> LENGTH: 30
<212> TYPE: DNA
<213> ORGANISM: Artificial Sequence
<220> FEATURE:
<223> OTHER INFORMATION: ChIP primers Sox2 R

<400> SEQUENCE: 53
caaagtttct tttattcgta tgtgtgagca                                   30
```

<210> SEQ ID NO 54
<211> LENGTH: 32
<212> TYPE: DNA
<213> ORGANISM: Artificial Sequence
<220> FEATURE:
<223> OTHER INFORMATION: ChIP primer Oct F

<400> SEQUENCE: 54
cgcctcgagt ggggaacctg gaggatggca ag					32

<210> SEQ ID NO 55
<211> LENGTH: 30
<212> TYPE: DNA
<213> ORGANISM: Artificial Sequence
<220> FEATURE:
<223> OTHER INFORMATION: ChIP primer Oct4 R

<400> SEQUENCE: 55
tataagcttg gggaaggaag gcgccccaag					30

<210> SEQ ID NO 56
<211> LENGTH: 17
<212> TYPE: DNA
<213> ORGANISM: Artificial Sequence
<220> FEATURE:
<223> OTHER INFORMATION: ChIP primers GAPDH F Primer

<400> SEQUENCE: 56
tccaagcgtg taagggt					17

<210> SEQ ID NO 57
<211> LENGTH: 18
<212> TYPE: DNA
<213> ORGANISM: Artificial Sequence
<220> FEATURE:
<223> OTHER INFORMATION: ChIP Primers GAPDH R Primer

<400> SEQUENCE: 57
gaagggactg agattggc					18

<210> SEQ ID NO 58
<211> LENGTH: 25
<212> TYPE: DNA
<213> ORGANISM: Artificial Sequence
<220> FEATURE:
<223> OTHER INFORMATION: Cloning Primers EpEX F

<400> SEQUENCE: 58
tataagctta ccatggcgcc cccgc					25

<210> SEQ ID NO 59
<211> LENGTH: 23
<212> TYPE: DNA
<213> ORGANISM: Artificial Sequence
<220> FEATURE:
<223> OTHER INFORMATION: Cloning primers EpEX R

<400> SEQUENCE: 59
cgcctcgaga ataaccagca caa					23

<210> SEQ ID NO 60
<211> LENGTH: 27
<212> TYPE: DNA
<213> ORGANISM: Artificial Sequence
<220> FEATURE:
<223> OTHER INFORMATION: Cloning primers EpCAM F

```
<400> SEQUENCE: 60
gataagctta tggcgccccc gcaggtc                                          27

<210> SEQ ID NO 61
<211> LENGTH: 36
<212> TYPE: DNA
<213> ORGANISM: Artificial Sequence
<220> FEATURE:
<223> OTHER INFORMATION: Cloning primers EpCAM R

<400> SEQUENCE: 61
gatctcgagt gcattgagtt ccctatgcat ctcacc                                36

<210> SEQ ID NO 62
<211> LENGTH: 9
<212> TYPE: PRT
<213> ORGANISM: Homo sapiens

<400> SEQUENCE: 62

Val Gly Ala Gln Asn Thr Val Ile Cys
1               5

<210> SEQ ID NO 63
<211> LENGTH: 19
<212> TYPE: PRT
<213> ORGANISM: Homo sapiens

<400> SEQUENCE: 63

Lys Pro Glu Gly Ala Leu Gln Asn Asn Asp Gly Leu Tyr Asp Pro Asp
1               5                   10                  15

Cys Asp Glu

<210> SEQ ID NO 64
<211> LENGTH: 12
<212> TYPE: PRT
<213> ORGANISM: Homo sapiens

<400> SEQUENCE: 64

His Gly Thr Gln Met Thr Trp Trp Asp Pro Asp Leu
1               5                   10

<210> SEQ ID NO 65
<211> LENGTH: 12
<212> TYPE: PRT
<213> ORGANISM: Homo sapiens

<400> SEQUENCE: 65

Met Gln Gly Lys Asp Trp Met Asp Leu Ser Pro Thr
1               5                   10

<210> SEQ ID NO 66
<211> LENGTH: 12
<212> TYPE: PRT
<213> ORGANISM: Homo sapiens

<400> SEQUENCE: 66

Ser Thr Gln Met Ser Tyr Arg Asp Gln Asp Leu Tyr
1               5                   10

<210> SEQ ID NO 67
<211> LENGTH: 12
<212> TYPE: PRT
<213> ORGANISM: Homo sapiens
```

```
<400> SEQUENCE: 67

Val Pro Met Ser Arg Pro Glu Trp Asn Asp Leu Tyr
1               5                   10

<210> SEQ ID NO 68
<211> LENGTH: 12
<212> TYPE: PRT
<213> ORGANISM: Homo sapiens

<400> SEQUENCE: 68

Val Pro Val Gly Arg Leu Asp Phe Ile Asp Leu Tyr
1               5                   10

<210> SEQ ID NO 69
<211> LENGTH: 12
<212> TYPE: PRT
<213> ORGANISM: Homo sapiens

<400> SEQUENCE: 69

Thr Gln Lys Met Asp Ala His Asp Leu Tyr Pro Val
1               5                   10

<210> SEQ ID NO 70
<211> LENGTH: 12
<212> TYPE: PRT
<213> ORGANISM: Homo sapiens

<400> SEQUENCE: 70

Phe Gln Val Gly Asp Leu Tyr Asp His Met Trp Asn
1               5                   10

<210> SEQ ID NO 71
<211> LENGTH: 12
<212> TYPE: PRT
<213> ORGANISM: Homo sapiens

<400> SEQUENCE: 71

Trp Gln Asn Val Glu Tyr Asp Met Arg Glu Trp Ile
1               5                   10

<210> SEQ ID NO 72
<211> LENGTH: 12
<212> TYPE: PRT
<213> ORGANISM: Homo sapiens

<400> SEQUENCE: 72

Val Thr Pro Gln Ala Lys Asp Trp Tyr Thr Leu Tyr
1               5                   10

<210> SEQ ID NO 73
<211> LENGTH: 19
<212> TYPE: PRT
<213> ORGANISM: Homo sapiens

<400> SEQUENCE: 73

Lys Pro Glu Gly Ala Leu Gln Asn Asn Asp Gly Leu Tyr Asp Pro Asp
1               5                   10                  15

Cys Asp Glu
```